US009128097B2

(12) United States Patent
Skindersø et al.

(10) Patent No.: US 9,128,097 B2
(45) Date of Patent: Sep. 8, 2015

(54) METHOD AND KIT FOR ASSESSING VIABLE CELLS

(75) Inventors: Mette Elena Skindersø, Virum (DK); Helle Frobøse Sørensen, Copenhagen V (DK); Søren Kjærulff, Hillerod (DK)

(73) Assignee: ChemoMetec A/S, Allerød (DK)

( * ) Notice: Subject to any disclaimer, the term of this patent is extended or adjusted under 35 U.S.C. 154(b) by 739 days.

(21) Appl. No.: 13/003,943

(22) PCT Filed: Jul. 13, 2009

(86) PCT No.: PCT/DK2009/050173
§ 371 (c)(1),
(2), (4) Date: Sep. 2, 2011

(87) PCT Pub. No.: WO2010/006615
PCT Pub. Date: Jan. 21, 2010

(65) Prior Publication Data
US 2011/0312012 A1    Dec. 22, 2011

(30) Foreign Application Priority Data
Jul. 14, 2008  (DK) .................................. 2008 00989

(51) Int. Cl.
*C12Q 1/02* (2006.01)
*G01N 33/58* (2006.01)
(Continued)

(52) U.S. Cl.
CPC .............. *G01N 33/583* (2013.01); *C09B 15/00* (2013.01); *C09B 57/00* (2013.01); *C09B 57/02* (2013.01); *G01N 33/502* (2013.01)

(58) Field of Classification Search
CPC .............. G01N 15/14; G01N 21/6428; C12Q 1/00–1/02; A61K 31/37; C07D 207/448
See application file for complete search history.

(56) References Cited

U.S. PATENT DOCUMENTS

2004/0248107 A1    12/2004  Sokolova et al.

FOREIGN PATENT DOCUMENTS

EP    0 601 606    6/1994
EP    0 753 732    1/1997
(Continued)

OTHER PUBLICATIONS

Margaret E. Langmuir, Jun-Rui Yang, Adel M. Moussa, Richard Laura and Karen A. LeCompte, New Naphthopyranone Based Fluorescent Thiol Probes, 1995, Tetrahedron Letters, vol. 36, No. 23, pp. 3989-3992.*

(Continued)

*Primary Examiner* — Blaine Lankford
*Assistant Examiner* — Trent Clarke
(74) *Attorney, Agent, or Firm* — Gifford, Krass, Sprinkle, Anderson & Citkowski, P.C.

(57) ABSTRACT

The present invention provides simple, rapid methods and procedures for analyzing cells, hereunder quantitative and qualitative assessment of cells, such as viability. The present invention relates to the use of various optionally substituted reporter compounds particularly detectable upon their reaction with thiol-containing species present in higher concentrations in intact (e.g., living) cells than in non-intact (e.g., dead, stressed and apoptotic) cells. The present invention also relates to the use of various optionally substituted reporter compounds particularly detectable upon their reaction with species present in intact and/or non-intact cells. Moreover, the present invention relates to the use of measuring techniques and/or instruments coupled with the use of various optionally substituted reporter compounds. The invention further relates to compositions used in methods for analyzing cells, such as a composition comprising N-(7-dimethylamino-4-methyl-3-coumarinyl)-maleimide (DACM).

19 Claims, 27 Drawing Sheets

(51) Int. Cl.
*C09B 15/00* (2006.01)
*C09B 57/00* (2006.01)
*C09B 57/02* (2006.01)
*G01N 33/50* (2006.01)

(56) References Cited

FOREIGN PATENT DOCUMENTS

| WO | WO 98/37226 | 8/1998 |
|---|---|---|
| WO | WO 98/50777 | 11/1998 |
| WO | WO 0028297 | 5/2000 |
| WO | WO 01/77648 | 10/2001 |
| WO | WO 2008/157003 | 12/2008 |

OTHER PUBLICATIONS

B. J. Shenker, J. S. Mayro, C. Rooney, L. Vitale, and I. M. Shapiro, Immunotoxic Effects of Mercuric Compounds on Human Lymphocytes and Monocytes. IV. Alterations in Cellular Glutathione Content, 1993, Immunopharmacology and Immunotoxicology, 15(2&3), 273-290.*

Antonio Macho, Tamara Hirsch, Isabel Marzo, Philippe Marchetti, Bruno Dallaporta, Santos A. Susin, Naoufal Zamzami, and Cuido Kroemer, Glutathione Depletion Is an Early and Calcium Elevation Is a Late Event of Thymocyte Apoptosis, 1997, The Journal of Immunology, vol. 158: pp. 4612-4619.*

Hiroaki Takahashi, Yasunori Nara and Katura Tuzimura, Fluorometric Determination of Glutathione by N-(9-Acridinyl)maleimide and Its Application to Biological Materials, 1978, Agric. Biol. Chem., 42 (4), pp. 769-774.*

'Propidium Iodide' pdf accessed from http://probes.invitrogen.com/media/pis/mp01304.pdf on Aug. 23, 2013.*

J. Antonie Maassen, Ton P.G.M. Thielen, and Wim Moller, Synthesis and Application of Two Reagents for the Introduction of Sulfhydryl Groups into Proteins, 1983, Eur. J. Biochem., vol. 134, pp. 327-330.*

Alt Zantema, J. Antonie Maassen, Jan Kriek, and Wim Moller, Preparation and Characterization of Fluorescent 50S Ribosomes. Specific Labeling of Ribosomal Proteins L7/L12 and L10 of *Escherichia coli*, 1982, Biochemistry, vol. 21, pp. 3069-3076.*

P. Chaussepied and M. F. Morales, Modifying preselected sites on proteins: The stretch of residues 633-642 of the myosin heavy chain is part of the actin-binding site, 1988, Proc. Nati. Acad. Sci. USA, vol. 85, pp. 7471-7475.*

NPL document 'DACM sources', a list of commercial sources for CAS registry No. 55145-14-7 from SciFinder accessed Dec. 19, 2014.*

Akasaka et al., 1990, "Fluorometric determination of sulfite in wine by N-(9-acridinyl)maleimide", Agric. Biol. Chem., 54, 2, pp. 501-504.

Baranowska-Kortylewicz et al., 1993, "Labeling of sulfhydryl groups in intact mammalian cells with coumarins", ioconjugate Chemistry, vol. 4, No. 4, pp. 305-307.

Durand et al., 1983, "Flow cytometry techniques for studying cellular thiols", Radiation Research, 95, pp. 456-470.

Evenson et al., 1989, "Flow cytometric analysis of rodent epididymal spermatozoal chromatin condensation and loss of free sulfhydryl groups", Molecular Reproduction and Development, vol. 1, No. 4, pp. 283-288.

Fu et al, 2005, ."Spectrofluorimetric determination of thiols in biological samples with a new fluorescent probe 3-maleimidylbenzanthrone", Analytical Letters, 38, pp. 791-802.

Hansen et al., 1996, "Inactivation of MET10 in brewers yeast specifically increases SO2 formation during beer production", Nature Biotech, 14, pp. 1587-1591.

Kamata et al., 1993, "A sensitive fluorometric assay of glutathione reductase activity with N-(9-acridinyl)maleimide", Analytical Sciences, vol. 9, No. 6, pp. 867-870.

Kanda et al., 1998, "Histone-GFP fusion protein enables sensitive analysis of chromosome dynamics in living mammalian cells", Curr Biology, 8, pp. 377-385.

Kobayashi et al, 1994, "Possible role of metallothionein in the cellular defense mechanism against UVB irradiation in neonatal human skin fibroblasts", Photochemistry and Photobiology, vol. 59, No. 6, pp. 650-656.

Lutz et al., 1999, An advanced culture method for generating large quantities of highly pure dendritic cells from mouse bone marrow. J Immunol Methods 223, pp. 77-92.

Moreno et al., 1991, "Molecular genetic analysis of fission yeast Schizosaccharomyces pompe", Methods Enzym, 194, pp. 795-823.

Odom et al., 1990, "Movement of tRNA but not the nascent peptide during peptide bond formation on ribosomes", Biochemistry, vol. 29, No. 48, pp. 10734-10744.

Olive et al, 1982, "Characterization of the uptake and toxicity of a fluorescent thiol reagent", Cytometry, Alan Liss, New York, US, vol. 3, No. 5, pp. 349-353.

Poot et al., 1991, "Flow cytometric analysis of cell cycle-dependent changes in cell thiol level by combining a new laser dye with hoechst 33342", Cytometry, Alan Liss, New York, US, vol. 12, No. 2, pp. 184-187.

Rice et al., 1986, "Quantitative analysis of cellular glutathione by flow cytometry utilizing monochlorobimane: Some applications to radiation and drug resistance in vitro and in vivo", Cancer Research, 46, pp. 6105-6110.

Seibel et al., 2007, "Nuclear localization of enhanced green fluorescent protein homomultimers", Anal Biochem, 368, pp. 95-99.

Sippel, 1981, "New fluorochromes for thiols: maleimide and iodoacetamide derivatives of a 3-phenylcoumarin fluorophore". J Histochem Cytochem., 29(2), pp. 314-316.

Styrkarsdottir et al., 1993, "The smt-0 mutation which abolishes mating-type switching in fission yeast is a deletion", *Curr Genet*, 23, pp. 184-186.

Yokoi et al., 1984, "Immuno cytochemical detection of desmin in fat storing cells ito cells", Hepatology, vol. 4, No. 4, pp. 709-714.

Østergaard et al., 2004, "Monitoring disulfide bond formation in the eukaryotic cytosol", J Cell Biol, vol. 166, 3, pp. 337-345.

Skindersoe, et al., A Novel and Rapid Apoptosis Assay Based On Thiol Redox Status, Journal of the International Society For Advancement of Cytometry, 2012, pp. 1-7, Wiley Online Library (wileyonlinelibrary.com).

* cited by examiner

A

B

METHOD AND KIT FOR ASSESSING VIABLE CELLS

CROSS-REFERENCE TO RELATED APPLICATIONS

This application is the U.S. national phase of PCT/DK2009/050173 filed Jul. 13, 2009, which claims priority of Danish Patent Application No. PA 2008 00989 filed Jul. 14, 2008.

All patent and non-patent references cited in the application, or in the present application, are also hereby incorporated by reference in their entirety.

FIELD OF INVENTION

The present invention provides simple, rapid methods and procedures for analyzing cells, hereunder quantitative and qualitative assessment of cells. The present invention relates to the use of various optionally substituted reporter compounds particularly detectable upon their reaction with species (e.g., sulphur-containing species, hereunder thiol-containing species) present in higher concentrations in intact (e.g., living) cells than in non-intact (e.g., necrotic, stressed and apoptotic) cells. The present invention also relates to the use of various optionally substituted reporter compounds particularly detectable upon their reaction with species present in intact and/or non-intact cells. Moreover, the present invention relates to the use of measuring techniques and/or instruments coupled with the use of various optionally substituted reporter compounds. The invention further relates to compositions used in methods for analyzing cells.

BACKGROUND OF INVENTION

Characterizing cell viability and other cell features can provide useful information with respect to a wide range of applications. However, methods presently employed are quite complex and time consuming. Existing methods make use of permeable fluorophores with an attached ester linker that is subsequently cleaved when present in cells and thereafter emits fluorescens. This technique has however drawbacks including extended incubation times (several minutes).

SUMMARY OF INVENTION

The present invention provides a general strategy for rapid analysis of viable and/or healthy cells. The invention relates to methods including labelling agents that are freely taken up by cells and capable of reacting with intracellular thiols (e.g., —SH in cysteine-containing peptides such as glutathione). Since the labelling agents essentially react instantly with intracellular thiols no incubation time is required for measurement of viability and/or healthiness. It has been found that the intracellular concentration of thiols reflects the viability and/or healthiness of the cell. Hence, necrotic and apoptotic cells contain low to intermediate amounts of thiols, whereas viable, healthy cells contain high amounts of thiols. Viable intact cells comprises thiols in so high amounts that it is possible to detect the cells using a labelling agent reacting with the thiols, whereas dead cells comprises no or so little amount of thiols that they are not detectable using the labelling agents according to the invention. In particular the labelling agents comprises a label that is activated, ie. visible in the system used, only after the reaction with the thiols have taken place. Thereby only the cells comprising thiols are made visible in the system used.

Accordingly, in one aspect the invention relates to a method for quantitative or qualitative assessment of viable cells providing a biological sample
  adding a labelling agent to said biological sample, wherein said labelling agent comprises a compound capable of reacting with one or several thiol groups.
  reacting said labelling agent with said biological sample obtaining a labelled biological sample,
  assessing viable cells in the labelled biological sample.

In another aspect the invention relates to a method for quantitative or qualitative assessment of apoptotic cells
  providing a biological sample
  adding a labelling agent to said biological sample, wherein said labelling agent comprises a compound capable of reacting with one or several thiol groups.
  reacting said labelling agent with said biological sample obtaining a labelled biological sample,
  assessing apoptotic cells in the labelled biological sample.

In one embodiment of the invention, improved detection of intact cells according to the present invention results from a process involving reaction of a labelling agent being a virtually non-fluorescent maleimide-substituted reporter molecule which become fluorescent upon reaction with intracellular thiols.

Thus, in a preferred embodiment the methods according to the invention in general involve the use of a labelling agent having the form

CC-REPORTER wherein CC is a group selected to be reactive in the presence of thiols, and upon such reaction change the optical and/or spectral properties of the REPORTER. After the CC-group reacts with the intracellular analyte (or species) the REPORTER is made detectable by the change in optical and/or spectral properties.

It has further been found that thiols (e.g., cysteine —SH groups in glutathione or other peptides or proteins) could be oxidized to disulphides by oxygen present in cells. In living cells the enzyme machinery could be capable of reducing disulphides back to thiols. In dead cells, however, the enzyme machinery indicates that this is not working and as a result thiol concentrations are much lower than in living cells.

Moreover, it has been found, that a decrease in cellular thiols may precede cell death. It has for example been found that apoptotic cells have a lower level of cellular thiols compared to healthy cells, due to increased efflux of the main cellular thiol glutathione. Thus the cellular thiol level may also reflect the spectrum of viability; highly viable cells having a high level of thiols while apoptotic cells have an intermediate level of thiols and nonviable cells has a low thiol level (see FIG. 25).

It has been found that when a REPORTER, such as a fluorogen covalently bound to a CC group such as a maleimide group (c.f., 2) was introduced into a cell, then its latent

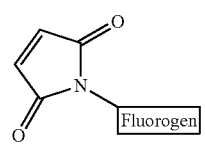

fluorescence might only—or at least to a greater extent—be realized in a living cell due to the higher concentration of thiols than in dead cells. Further, a fine-tuning of the reactivity of the maleimide group towards different types of thiols (e.g., various more or less sterically hindered thiols and/or aromatic —SH versus alkyl —SH and/or —SH bound to more or less electron-donating and/or electron-withdrawing groups) may be obtained using maleimide groups substituted at their C2=C3 double bond (c.f., e.g., 3 in which either one or both of R1 and R2 optionally can be more or less sterically hindered substituents and/or aromatic or alkyl substituents and/or more or less

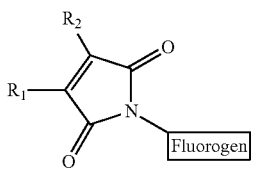

3 electron-donating and/or electron-withdrawing groups). This will allow discrimination between the presence and/or concentration of different types of thiols in the cell or compartments of the cell. All of the above information—either alone or in combination—will allow the determination or estimation of the state of condition of a cell, hereunder the health and metabolic and proliferating state of a cell as well as the cell type, for instance to distinguish cells of bacterial, plant or animal origin.

In another aspect the invention relates to a kit for quantitative or qualitative assessment of viable cells comprising a labelling agent as defined above and instructions for reacting said labelling agent with a biological sample.

Furthermore, the invention relates to a method for quantitative or qualitative assessment of cells provinding a biological sample comprising the cells to a sample domain, adding a labelling agent to said biological sample, wherein said labelling agent comprises a compound capable of reacting with one or several thiol groups in the cells, and reacting said labelling agent with said biological sample obtaining a labelled biological sample, exposing, onto an array of active detection elements, an at least one-dimensional spatial representation of electromagnetic signals having passed from the domain, the representation being one which is detectable as an intensity by individual active detection elements, under conditions which will permit processing of the intensities detected by the array of detection elements during the exposure in such a manner that representations of electromagnetic signals from the biological particles are identified as distinct from representations of electromagnetic signals from background signals, and preferably wherein the spatial image exposed onto the array of active detection elements is subject to such a linear enlargement that the ratio of the image of a linear dimension on the array of detection elements to the original linear dimension in the exposing domain is smaller than 20:1, processing the intensities detected by the detection elements in such a manner that signals from the biological cells are identified as distinct from background signals, and based on the results of the processing obtaining a quantitative or qualitative assessment of the cells.

In one aspect the methods according to the invention involve the use of N-(7-dimethylamino-4-methyl-3-coumarinyl)-maleimide (DACM). In particular, the invention relates to a composition for assessing a sample comprising cells, wherein said composition comprises DACM.

DETAILED DESCRIPTION OF THE INVENTION

Figure 1:
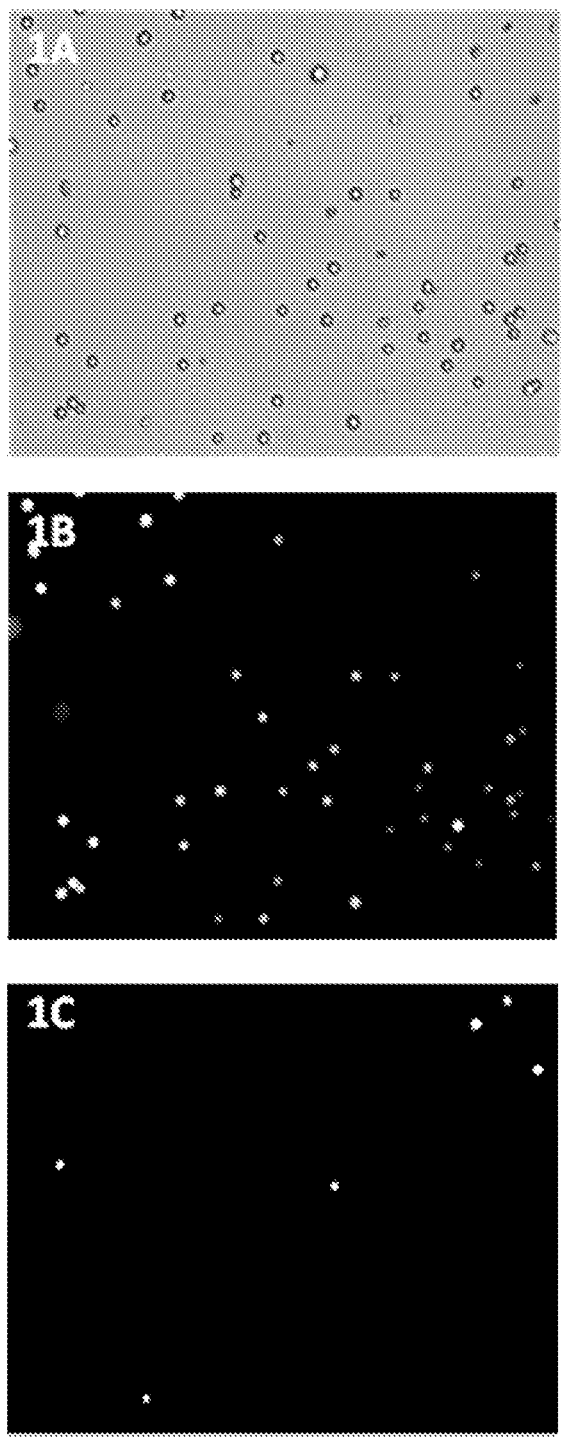
FIG. 1: 1A) Phase contrast image of proliferating Jurkat cells. 1B) The same cells as 1A) were micrographed using a UV band pass filter cube, thereby showing the NAM (4) stained cells. 1C) The same cells as 1A) were micrographed using a green long pass filter cube, thereby showing the PI stained cells. (10× magnification).

The present invention relates to the use of compounds capable of reacting with one or several thiol groups within living cells for assessing viable cells as well as for distinguishing living cells from dead cells, as well as providing detailed information about the cells, such as apoptosis and stress/health status. Accordingly, in one embodiment determination of cell viability includes metabolic activity, metabolite quantification, cell division, proliferation, health, stress level, apoptosis, necrosis or other state of condition.

Furthermore, in one embodiment the invention relates to determination of cell viability, in particularly includes determination of mobility and/or quantification of viable cells.

The term cell viability is used in its normal meaning, ie. a determination of living or dead cells, based on a total cell sample. A number of analysis of the viable cells may be performed, such as quantification of the viable cells, determination of mobility of the cells, or for example determination of morphology of viable cells, localisation of viable cells etc. For example cell viability counts have a tremendous number of applications. Cell viability measurements may be used to evaluate the death or life of a specific cell type, such as for example cancerous cells, in other applications cell viability tests might calculate the effectiveness of a pesticide or insecticide, or evaluate environmental damage due to toxins, see also below with respect to examples of samples.

Testing for cell viability usually involves looking at a sample cell population and staining the cells to show which are living and which are dead.

It has been found that the labelling agent according to the invention is particularly effective in staining living cells only thereby offering the opportunity of distinguishing living cells from dead cells in a sample. A great advantage of the present invention is the fast result obtained.

The term cell mobility generally refers movements of the cell, such as cell motility as well as cell differentiation and cell proliferation, wherein motility generally refers to the ability of some cells to move spontaneously and actively, such as sperm cells, propelled by the regular beat of their flagellum, or the bacterium *E. coli*, which swims by roting a helical prokaryotic flagellum.

As shown in the Examples the labelling agent is present in the nucleus as well as the cytosol of the cell.

Samples

The sample may be any sample, such as a biological sample, comprising cells for which viability should be determined. The method according to the invention applies to analysis of any type of cell or biological material or tissue, including the raw materials and processes associated with the manufacture, storage and transportation of said products, for the presence of viruses, bacteria, fungi, protozoa or components of these organisms.

In particular a biological sample may be selected from a body fluid sample, a tissue sample, a fermentation sample, a liquid cultivation sample, a cell culture sample, a water sample, such as mammalian and yeast cell cultures, a beverage sample, a pharmaceutical sample, a microelectronic product, and cells suspended in a liquid. More particular the biological sample is selected from a blood sample, a urine sample, a saliva sample, a semen sample, a solubilised tissue sample, a milk sample, or selected from a liver sample, a kidney sample, a muscle sample, a brain sample, a lung sample.

The biological sample may be selected from any species, such as a human sample, a mouse sample, a rat sample, a monkey sample, a dog sample Furthermore, the sample may be selected from a culture of cells, such as a bacterial culture, a mammalian cell culture, a protozoa culture or other cell cultures.

The biological material can be taken from raw material and processes associated with the manufacture, storage and transportation of said biological material.

Thiol-Reacting Compound

The labelling agent according to the invention comprises a group capable of reacting with one or several thiol groups within the cells as discussed above. The thiol-reacting compound may be any suitable compound, and in particular the compound is selected from the group consisting of maleimide compounds, bimane compounds, haloacetamide compounds. The labelling agent passes freely the cell membrane, ie. is capable of passing the cell membrane of living cells, and thereby react with intracellular thiols.

The thiol-reacting compounds preferably has a fluorescent or aromatic groups directly attached to it or indirectly via a covalently bound linker. The fluorescent group may be selected from fluorone, rhodamine, acridine, cyanine, thionine, safranine, coumarin and phenanthridine. In particular, the fluorone fluorescent group is selected from CFDA-SE, CFSE, calcein, carboxyfluorecein, eosin, erythrosine, fluorescein, fluorosceine amidite, fluoroscein isothiocyanate, Indian yellow or merbromin. Furthermore, in one embodiment the rhodamine fluorescent group is selected from rhodamine, sulforhoadmine 101, sulforhodamine B or Texas red. In another embodiment, the acridine fluorescent group is selected from acridine orange or acridine yellow. In yet another embodiment the cyanine fluorescent group is selected from DiOC6 or SYBR green. In a further embodiment the phenanthridine fluorescent group is selected from ethidium bromide or propidium iodide.

Furthermore, the fluorescent or aromatic groups may be substituted with substituents thereby increasing or reducing their water solubility and/or ability to be taken up by the sample. In another embodiment, the fluorescent or aromatic groups may be substituted with substituents that change their optical or spectral properties, allowing control over the flexibility and specificity needed in a particular study or analysis.

In particular the aromatic group is selected from phenyl, naphtyl, anthracene, acridine fluorine, pyridine, pyrimidine, purine or indole.

In a preferred embodiment the invention is further directed to a maleimide compound, said maleimide compound having the following formula (5):

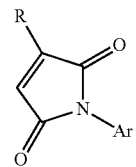

5 or the following formula (5A):

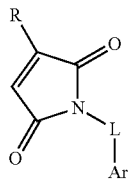

5A wherein: R is $R_a$ or $OR_a$ and $R_a$ is H, $C_1$-$C_8$ alkyl, $CH_2CO_2H$, $CH_2CH_2OH$ or CN and L is a spacer sequence that includes $C_1$-$C_4$ alkyl, $OCH_2CH_2O$, $NHCO(C_1$-$C_4H_2$ alkyl)NHCO, $CONH(C_1$-$C_4H_2$ alkyl)NHCO, $NHCO(C_1$-$C_4H_2$ alkyl)CONH, $CONH(C_1$-$C_4H_2$ alkyl)CONH and Ar is a rigid aromatic skeleton comprising one to six fused aromatic rings such as phenyl, naphthyl, anthracene, acridine, fluorene, pyridine, pyrimidine, purine, or indole etc., wherein the maleimide group is positioned around—or conjugated directly to—the aromatic core, and including fluorescent aromatic derivatives such as fluorescein, rhodamine, eosin, thionine, safranin or coumarin; or said maleimide group has the following formula (6):

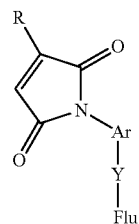

6 or (6A):

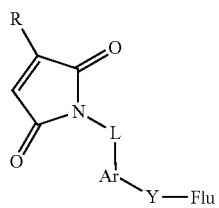

6A wherein: R is $R_a$ or $OR_a$ and $R_a$ is H, $C_1$-$C_8$ alkyl, $CH_2CO_2H$, $CH_2CH_2OH$ or CN, L is a spacer sequence that includes $C_1$-$C_4$ alkyl, $OCH_2CH_2O$, $NHCO(C_1$-$C_4H_2$ alkyl)NHCO, $CONH(C_1$-$C_4H_2$ alkyl)NHCO, $NHCO(C_1$-$C_4H_2$ alkyl)CONH, $CONH(C_1$-$C_4H_2$ alkyl)CONH and Ar is a rigid aromatic skeleton comprising one to six fused aromatic rings such as phenyl, naphthyl, anthracene, acridine, fluorene, pyridine, pyrimidine, purine, or indole etc. Y is a spacer sequence that includes a single bond, $C_1$-$C_4$ alkyl, $OCH_2CH_2O$, NHCO ($C_1$-$C_4H_2$ alkyl)NHCO, $CONH(C_1$-$C_4H_2$ alkyl)NHCO, $NHCO(C_1$-$C_4H_2$ alkyl)CONH, $CONH(C_1$-$C_4H_2$ alkyl) CONH, and Flu is a fluorophore such as fluorescein, rhodamine, eosin, thionine, safranin, and coumarin.

In some preferred embodiments of the invention compounds according to formula 6 or 6A provide a strategy for introducing substituent effects (eg. reducing or increasing water solubility or uptake by the sample) via the aromatic core Ar (which optionally may be non-fluorescent) without significantly altering the fluorescent properties of the fluorophore Flu.

In one preferred embodiment the labelling agent comprises N-(9-acridinyl)maleimide (cf. formula 4)

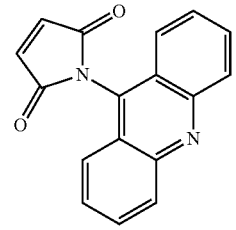

4

In a more preferred embodiment the N-(9-acridinyl)maleimide is present in low concentration in aqueous solution optionally containing small amounts of dimethyl sulfoxide (DMSO). The Examples show the results demonstrating the markedly superior fluorescence from living cells exposed to 4 as compared with dead cells exposed to 4.

Application of N-(9-acridinyl)maleimide (NAM) (cf. 4) as a cell viability marker is described in Examples 1, 2 3, 8, 9 and 12 which show how viability of mammalian and insect cells can be determined using the invention. Using N-(9-acridinyl) maleimide (NAM) together with the impermeable stain propidium iodide (PI) it was shown that NAM solely stains PI negative cells. As only non-viable cells are permeable to PI, this observation implies that NAM is a viable stain.

In Example 4 it is demonstrated that the fluorescent properties of NAM changes in the presence of the —SH reagents reduced glutathione (GSH) and dithiothreitol (DTT), but not by oxidized glutathione (GSSG), suggesting that reacts with the thiol in GSH and DTT forming a fluorescent compound.

Using GFP as reporter it is demonstrated in Example 6 that (reduced) fluorescent NAM (N-(9-acridinyl), maleimide) localizes to the cytosol and nucleus in mammalian cell lines. Hence, the labeling agent is not a DNA specific stain and can be used for whole cell staining.

In another embodiment the labeling agent comprises the phenylcoumarine derivative CPM, another maleimide capable of reacting with thiols forming fluorescent compounds. In Example 5 it is shown that CPM can be used to determine cell viability in an approach similar to the one described for NAM.

In another preferred embodiment the labeling agent comprises N-(7-dimethylamino-4-methyl-3-coumarinyl)-maleimide (DACM, cf. formula 7).

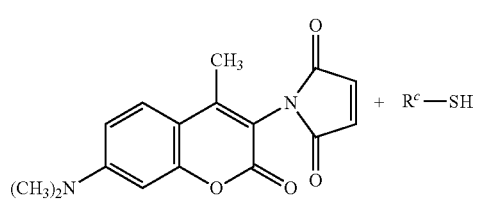

7

DACM M.W. = 298.30

Nonfluorescent

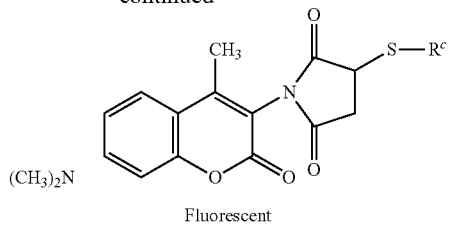

Fluorescent

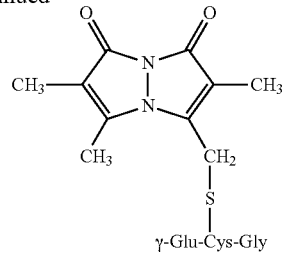

Fluorescent

Similar to NAM, DACM freely passes the cell membrane and reacts with intracellular thiols producing fluorescent compounds. In Examples 11, 15 and 16 it was demonstrated that DACM can be used for detecting changes in the intracellular level of thiols and, hence, for measuring viability of mammalian cells. In Example 15 it was furthermore shown that the intensity of DACM fluorescence correlates with phosphatidyl-serine flip-flop and depolarization of the mitochondrial membrane, two hallmarks of apoptosis. Thus, DACM can be used as an indirect measurement of apoptosis. In Example 16 it was demonstrated that DACM can be used as an indicator of overall stress/health status. Finally, in Example 17 it was established that DACM can be used for discriminating between living and dead yeast cells. In the two distantly related yeast species, *S. pombe* and *S. cerevisiae*, DACM preferably stains living cells.

In another preferred embodiment the thiol-reacting compound is a haloacetamide, such as bromoacetamides and iodoacetamides. Halocetamides readily react with all thiols including those found in proteins and peptides such as glutathione (GSH). During the reaction the halide is displaced and a thioether is formed. See the following reaction scheme:

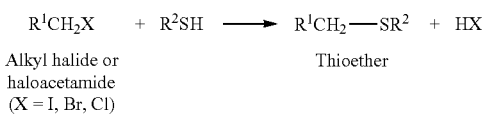

Even though the reaction mechanism between haloacetamide and thiol are different to the reaction between maleimide and thiol, both concepts can be used to quantify thiols and—as seen from example CPI—also the iodoacetamides can be used to measure cell viability.

In yet another preferred embodiment the thiol-reacting compound is a bimane compound, such as halide bimane compounds, in particular bromobimane, monobromotrimethylamminiobimane and chlorobimane. The bimanes are essentially non-fluorescent but becomes fluorescent after reaction with thiols. Without being bound by theory it is believed that the reaction is as in the following reaction scheme:

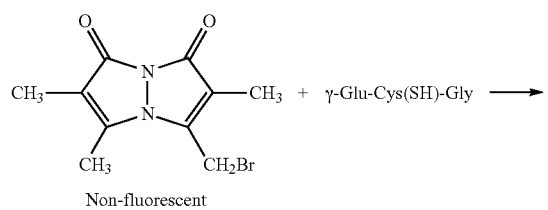

Non-fluorescent

Double Labelling

In one embodiment the determination of viability includes the labelling agent as discussed above capable of visualising viable cell as well as a labelling agent capable of exclusively labelling dead cells. Thereby the determination may be improved by applying one coloured label to living cells and another coloured label to dead cells improving the visibility of living cells as compared to dead cells. Thus, in one embodiment the cell viability can be determined from quantification of live and dead cells using propidium iodide (PI) to label dead cells and one of the labelling agents discussed above for labelling living cells, and thereby distinguish dead cell from live cells.

While a number of preferred embodiments have been described above, the present invention can be performed and exploited in a large number of ways and is not limited to a single assay or analysis but may be selected in accordance with the specific sample and cell type. In the following, a discussion of a number of measures and details relevant to the invention is given, comprising both preferred embodiments and embodiments which illustrate possibilities of working the invention.

The method according to the invention for determining viability of cells in a biological sample may be conducted in any suitable system and apparatus. Accordingly, the method according to the invention may be automated and tailored for monitoring in a microscope, in flow cytometry measurements, in cell counting devices such as instruments from ChemoMetec A/S, studied by cytochemistry etc., such as provided by the NucleoCounter family of instruments from ChemoMetec A/S, hereunder using low magnification and/or optionally disposable cassettes or other sample compartments (c.f., e.g., Hansen, F. E. R., Glensbjerg, M., Arnvidarson, B. & Jeppesen, J. M.: "A Method and a System for Determination of Cells in a Liquid", PCT/DK1998/0000175 (WO/1998/050777); cytochemistry for studying the locations, structural relationships, and interactions of eukaryotic or other cellular constituents (hereunder slide-based cytochemistry, i.e., on the surface of a microscope slide)

In a preferred embodiment the determination is conducted in a system comprising a sample domain wherein the biological sample is arranged and whereupon the signals from the viable cells are detected.

Sample domain.

The sample domain established according to the present invention may be a compartment or an equivalent thereof, wherein the sample is located during recording, such as a three-dimensional sample domain. The sample domain may be a part of a flow-through system, wherein each sample is part of a series of samples, whereby one sample is replacing the previous sample in the sample domain. In such embodiments, the sample compartment has both an inlet and an outlet. In other embodiments, the sample compartment only has an inlet.

In one particular embodiment the sample domain is part of a cassette, such as a disposable cassette as described in PCT/DK99/00605. In some embodiments, such a cassette contains pre-added chemicals that contribute to generation of the signal. The sample is contained in the interior of the sample compartment, which normally has an average thickness of between 20 µm and 200 µm, usually between 30 µm and 150 µm and in many practical embodiments between 50 µm and 100 µm.

The part of the sample domain allowing signals to be detected is referred to as the exposing window that can be as little as 1 mm$^2$ or more, preferably with an area of 2 mm$^2$ or more, preferably with an area of 4 mm$^2$ or more, preferably with an area of 10 mm$^2$ or more, preferably with an area of 20 mm$^2$ or more, preferably with an area of 40 mm$^2$ or more, more preferably with an area of 100 mm$^2$ or more.

Sample volume.

The optimal volume of the sample needed is highly dependent on the number of cells present in the sample and the predetermined statistical quality parameter sought.

Sample volumes may be from 0.005 µl up to several hundred milliliters.

Thus, in one embodiment the sample volumes are from 0.01 to 20 µl, but often a volume of more than 0.1 µl, more than 1.0 µl or even more than 10 µl is used. In another embodiment the sample volume is from 0.02 to 1 ml.

However, in other preferred embodiments of the present invention make it possible to assess cells from a considerably large volume of sample. This can allow the measurement of samples with only few cells of interest per volume of sample. Sample volumes larger than 1 ml and even larger than 100 ml can be used for the analysis, the volume being defined as the total volume of any liquid sample introduced into a sample domain, preferably to any flow system connected to the device, before the measurement of the sample.

Often the design of the sample compartment or the sample is such that the size of the volume of the liquid sample is sufficiently large to permit the assessment of the at least one quantity parameter or the at least one quality parameter to fulfil a predetermined requirement to the statistical quality of the assessment based on substantially one exposure, so that the image is recorded in one exposure.

In another embodiment the assessment of at least one quality parameter or at least one quantity parameter is obtained on the basis of more than one image, preferably two images, more preferably more than two images, more preferably more than four images. In these situations the images are recorded through two, three or more exposures. This can for instance be done to fulfil a predetermined requirement to the statistical quality.

Also, information about the changes in the image in course of time, such as in case of study of mobility, is used in the assessment of at least one quality parameter or at least one quantity parameter, and in such situations more than one exposure may be made.

A large volume of the sample is preferably measured by passing the volume of sample through a cell retaining means, such as a filter, electrical field, magnetic field, gravitational field, such means preferably being included in the device or can be arranged to interact with any sample within the device. The cell retaining means should preferably be able to retain substantially all cells present in a sample, or at least a substantially representative fraction of at least one type of cell present in the sample.

When the cells from a large sample are retained, those cells can be re-suspended in a volume which is less than the volume of sample passed through the cell retaining means.

In one embodiment more than one portion of the same sample material can be subjected to analysis by exposure to the detection system. This can be done by allowing the sample compartment to be moved, thus exposing a different portion of the sample compartment.

Fluorescence

In a preferred embodiment the labelling agent comprises a group capable of emitting fluorescent light. A system based on fluorescence is generally more sensitive than a chromogenic since fewer product molecules are necessary for providing enough electromagnetic radiation to visualise the cells.

A fluorescent label is preferably capable of emitting signals in the wavelength range of from 300 to 1200 nm when excited by excitation light, such as a wavelength between 300 nm to 800 nm, or between 300 nm to 400 nm, or between 400 nm to 500 nm, or between 500 nm to 600 nm, or between 600 nm to 700 nm, or between 700 nm to 800 nm. One preferred fluorescence method is the method of polarised fluorescence.

Excitation Light Source

Often light using any wavelength range, in particular any wavelength between 200 nm to 1700 nm is used for excitation of the labelling agent. In many embodiments of this invention the signals which are detected are attenuation of electromagnetic radiation, for instance caused by absorption or scattering, and in many preferred embodiments of this invention the signals which are detected are emitted from the cells or the samples, for instance emission of photoluminescence (e. g. fluorescence and/or phosphorescence) or Raman scatter, and in other embodiments of this invention the signals which are detected are caused by scatter. In many preferred embodiments of this invention electromagnetic radiation, such as UV or visible light is transmitted onto the sample, in order to give rise to photoluminescence.

The wavelength of the excitation light is selected in accordance with the fluorescent group of the labelling agent. In one embodiment the excitation light emits light having a wavelength between 200 nm to 800 nm, such as between 200 nm to 700 nm, such as between 200 nm to 300 nm, or between 300 nm to 400 nm, or between 400 nm to 500 nm, or between 500 nm to 600 nm, or between 600 nm to 700 nm.

The excitation light source is any suitable light source, such as a light emitting diode (LED), a gas laser, a solid state laser, a laser diode, a gas lamp, such as a xenon lamp, a thermal lamp, such as a halogen lamp, capable of emitting excitation light in the desired range, see above.

It is preferred to use a diverging excitation light, such as light emitting diodes for in a cost-effective manner to expose as large area as possible of the sample to the excitation light.

It may be preferred to use more than one light source for the purpose of increasing the flux of light onto the sample, for instance by using two or more light emitting diodes. It is also possible to use more than one light source where some of the light sources have different electromagnetic properties.

By the use of several LEDs the sample may be exposed to excitation light from several angles leading to a substantially optimal excitation of the sample, the light sources are preferably operated in such a way that all transmit substantially simultaneously.

However for some applications wherein at least a first and a second light source are arranged in the first excitation light means, the first light source having a different wavelength band than the second light source, the light sources may transmit in an alternating manner. By the use of two different light sources it is possible to obtain two different fluorescence signals from the sample. There is no upper limit to the number of LEDs used, but often as many as 30 LEDs are provided, such as up to 50 LEDs, for example up to 100 LEDs, such as up to 150 LEDs, for example up to 200 LEDs, such as 300 or more LEDs.

If a less diverging light source is used a diverging optical means may be arranged in the excitation light path to diverge the excitation light properly.

When using laser diodes as the excitation light the proper divergence may be accomplished by an arrangement of at least 4 laser diodes optionally provided with diverging means.

The incident angle of the excitation light is preferably in the range between 0° and 90°, to the optical axis of the detection system, more preferably between 0° and 60°, such as between 10° and 45° to provide a suitable excitation of the sample.

Magnification.

It has surprisingly been found that it is possible to detect the signals from the labelled cells, even at a rather small magnification such as a magnification less than ×20. At this magnification it has been found that it is possible to quantitatively or qualitatively assess the cells, such as wherein the assessment of cells includes determination of cell viability, such as includes determination of mobility, spatial orientation or morphology, or wherein the assessment of cells includes quantification of viable cells, and/or wherein the assessment of cells includes metabolic activity, metabolite quantification, cell division, proliferation, health, stress level, apoptosis, necrosis or other state of condition.

In some embodiments the invention is preferably carried out at a low magnification whereby it is possible to detect spots in a large volume in one or a few exposures. The magnification factor is preferably below 10, such as below 5, such as 4, more preferably below 4, such as 2, more preferably below 2, such as 1. The advantage of such low magnification are several, among other things increased area of observation and increased depth of focusing implying increased volume exposed to the detection device.

When the spots in question have dimensions which are comparable to the size of a detection element, it is often preferred to have magnification of about 1/1, thus focusing the image of any spot on any one or just few detection elements. This can under some conditions give favourable detection of any signal.

When analysing spots which have dimensions which are comparable to, or bigger than the detection elements used, it is often advantageous to reduce the size of the image of such spot, to a degree where the size of the image is comparable to the size of a detection element. Thus in one embodiment it is preferred that the magnification factor below 1, preferably below 0.9, such as 0.8, more preferably below 0.8 such as 0.6, more preferably below 0.6 such as 0.5.

In these situations it is preferred that the ratio of the size of a spot, to the size of the image of the cell on the array of detection elements is 1/1 or less, preferably less than 1/1 and higher than 1/100, more preferably less than 1/1 and higher than 1/40, more preferably less than 1/1 and higher than 1/10, more preferably less than 1/1 and higher than 1/4, more preferably less than 1/1 and higher than 1/2.

Thus, it is often preferred that the spatial representation exposed onto the array of detection elements is subject to such a linear enlargement that the ratio of the image of a linear dimension on the array of detection elements to the original linear dimension in the sample domain is smaller than 40:1, normally at the most 20:1, preferably smaller than 10:1 and in many cases even at the most 6:1 or even smaller than 4:1.

It is often preferred that the cells are imaged on at the most 25 detection elements, in particular on at the most 16 detection elements and more preferred at the most 9 detection elements, such as at the most 5 detection elements, or even on at the most 1 detection element. The larger number of elements per cell will provide more information on the individual cells, while the smaller number of elements per cell will increase the total count that can be made per exposure.

Statistics.

As mentioned above, the size of the volume is suitably adapted to the desired statistical quality of the determination. Thus, where the determination is the determination of the number of cells in a volume, or the determination of the size and/or shape of cells, the size of the volume of the liquid sample is preferably sufficiently large to allow identification therein of at least two of the cells. More preferably, the size of the volume of the liquid sample is sufficiently large to allow identification therein of at least four of the cells. This will correspond to a repeatability error of approximately 50%. Still more preferably, the size of the volume of the liquid sample is sufficiently large to allow identification therein of at least 10 of the cells. This will correspond to a repeatability error of approximately 33%. Even more preferably, the size of the volume of the liquid sample is sufficiently large to allow identification therein of at least 50 of the cells. This will correspond to a repeatability error of approximately 14%. Evidently, where possible, it is preferred to aim at conditions where the size of the volume allows identification of even higher numbers. Thus, when the size of the volume of the liquid sample is sufficiently large to allow identification therein of at least 100 of the cells, it will correspond to a repeatability error of approximately 10%, and when the size of the volume of the liquid sample is sufficiently large to allow identification therein of at least 1000 of the cells, it will correspond to a repeatability error of as low as approximately 3%.

Stand still.

In a preferred embodiment of the invention the cells being assessed are at stand still or substantially at stand-still during analysis, thus allowing the optimal use of measurement time in order to improve any signal to noise conditions. This arrangement also eliminates any error which could be inherent in the assessment of cells caused by variation in flow conditions, particularly when an assessment of a property is a volume related property such as the counting of cells in a volume of sample.

Flow system.

The introduction of cell and reagent material into the sample domain may be provided by means of a flow system. The flow system may provide at least one of several operations to be carried out on the samples, said operations being selected from but not limited to transport, mixing with reagent, homogenising of sample and optionally reagent, heat treatment, cooling, sound treatment, ultra sound treatment, light treatment and filtering.

The sample in the device can be flown by the means of a flow system, which can be driven by a pump or a pressurised gas, preferably air, or by causing a pressure difference such that the pressure on the exterior of the inlet is higher than the pressure within at least a part of the system thus forcing the sample to flow through the inlet or by propelling means. In many embodiments of the present invention the flow in said flow system is controlled by one or more valves which can adjust the flow speed of the sample, see for example the flow systems described in PCT/DK98/000175.

Detection device.

The image which can be detected from the sample can for instance be detected by an array of detection elements, the array of detection elements comprising individual elements, each of which is capable of sensing signals from a part of the sample area, the array as a whole preferably being capable of sensing signals from substantially all of the sample area, or at least a well defined part of the sample area. The array of detection devices may for example be a one-dimensional array or a two-dimensional array. In order to facilitate the assessment of cells the intensities detected by the array of detection elements are processed in such a manner that representations of electromagnetic signals from the cells are identified as distinct from representations of electromagnetic background signals.

The detection means may comprise any detectors capable of sensing or detecting the signal emitted from the sample such as a fluorescence signal.

In a preferred embodiment detection means comprises a detector being an array of detecting devices or detection elements, such as a charge coupled device (CCD) the CCD may be a full frame CCD, frame transfer CCD, interline transfer CCD, line scan CCD, an eg. wavelength intensified CCD array, a focal plane array, a photodiode array or a photodetector array, such as a CMOS. The CMOS is preferably a CMOS image sensor with on-chip integrated signal condition and/or signal processing. Independent of the choice of any of the above detection devices the detection means may further comprise a white/black or colour CCD or CMOS.

Furthermore, the detection device may be included in a scanning microscope, such as a confocal scanning microscope.

Focusing-Lenses.

The inclusion of a focusing device for the focusing of a signal from the sample onto the detection elements in such a manner as to maximise the collection angle, the collection angle being defined as the full plane angle within which a signal is detected, has in many situations been found to give improved conditions for an assessment.

The collection angle of a focusing arrangement used can have effect on the intensity of any signal collected on the array of detection elements. When high sensitivity is needed it is therefore practical to increase the collection angle. The preferred size of the collection angle can also be determined by other requirements which are made to the system, such as focusing depth. In these situations the collection angle of the focusing means is preferably at least 2 degrees, preferably more than 5 degrees, more preferably more then 15 degrees, more preferably more than 20 degrees, more preferably more than 50 degrees, more preferably more than 120 degrees, more preferably more than 150 degrees.

Signal.

The signals measured from one or more detection elements may be corrected for systematic or varying bias by the use of a calculating means, the bias correction being accomplished by the use of one or more pre-defined value(s), preferably where each measured signal for one or more detection elements in said array of detection elements has one or more pre-defined value(s), more preferably where each pre-defined value is determined on the bases of one or more of any previous measurements.

The bias correction may be performed by subtracting the results obtained in one or several of other measurements from the measured signal, preferably where the other measurements are one or several of measurements of the same sample, or sample material, more preferably where the other measurement is the measurement taken previously of the same sample or sample material.

Processor.

Information of the signals detected by the detection means are input into a processor for processing, displaying and optionally storing the information.

The at least one quality or at least one quantity parameter of the cells is obtained by processing of the signals detected by the detection means. This processing can e.g. include conversion of the raw data using a pre-determined algorithm to obtain the quality or quantity parameter. The processing can also include use of a calibration curve or standard curve that specifies the relationship between the signal and the parameter of interest.

The signal information may be displayed on a display connected to the processor and/or printed. The information displayed may be any kind of information relating to the signals measured and/or the system used, such as a number, size distribution, morphology, classification of cells, excitation wavelength, emission wavelength, magnification. In particular the data processing means is capable of distinguishing partially overlapping areas of product.

EXAMPLES

Example 1

Use of NAM to determine viability of proliferating Jurkat (JM) cells (a T lymphocyte cell line)

Materials and Methods. Jurkat (JM) cells were grown at 37° C. in a humidified air atmosphere with 5% $CO_2$ in RPMI (Invitrogen, #61870) supplemented with 10% heat-inactivated fetal bovine serum (Invitrogen, #10108-165). 90 µL proliferating Jurkat cells (cell density $1.2 \times 10^6$, 99% viable determined using the NC-100 NucleoCounter system following the manufacturer's (ChemoMetec A/S) protocol) were added 10 µL NAM (N-(9-acridinyl)maleimide, Sigma, #01665, CAS no. 49759-20-8) dissolved in DMSO (100 µg NAM pr. mL DMSO) and mixed by pipetting. Cells were loaded into a NucleoCassette, containing the DNA stain propidium iodide (PI). The cells were investigated using an Olympus IX50 fluorescence microscope, and images were captured using a Lumenera CCD camera and in-house developed software. PI and NAM fluorescence were detected using, respectively, U-MWG2 (green long pass: 510-550 nm) and U-MNUA2 (UV band pass, 330-385 nm) filter cubes (Olympus).

Results. Observing the NAM stained cells under a fluorescence microscope using a UV filter it was clear that nearly all cells in the proliferating Jurkat cell culture were stained by NAM; only exception were PI positive cells (observed using the green long pass filter). (See 1A-1C in FIG. 1). Thus, PI and NAM seem to be complementary stains. As PI solely stains cells with disrupted plasma membrane (dead cells), this indicates that NAM stains cells with intact plasma membrane (live cells).

Example 2

Use of NAM to determine viability of HEK293 cells (a Human Embryonic Kidney cell line)

Materials and Methods. HEK293 cells were grown at 37° C. in a humidified air atmosphere with 5% $CO_2$ in DMEM (Invitrogen, #31966) supplemented with 10% heat-inactivated fetal bovine serum (Invitrogen, #10108-165). Cells were harvested with 0.5 mL of trypsin (Invitrogen, #25300) and neutralized with 5 mL medium (DMEM+10% FCS) two days after they had reached full confluency. These outgrown HEK293 cells (cell density $1.6 \times 10^6$, 78% viable determined using the NC-100 NucleoCounter system following the manufacturer's (ChemoMetec) protocol) were stained with 10 µg/mL NAM (Sigma, #01665). Another cell sample were treated with 0.25% Triton X-100 (Sigma, #T9284) and here-after added 10 μg/mL NAM. After staining, each cell sample was loaded into a NucleoCassette, containing the DNA stain propidium iodide (PI). The cells were investigated using an Olympus IX50 fluorescence microscope, and images were captured using a Lumenera CCD camera and in-house developed software. PI and NAM fluorescence were detected using, respectively, U-MWG2 (green long pass: 510-550 nm) and U-MNUA2 (UV band pass, 330-385 nm) filter cubes (Olympus).

Figure 2:
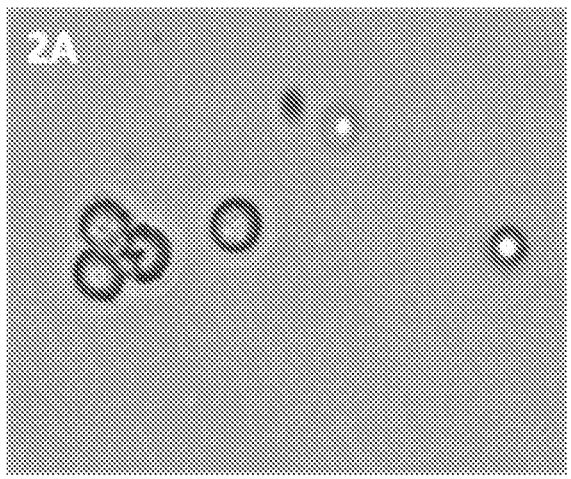
FIG. 2: 2A) Phase contrast image of HEK293 cells. 2B) The same cells as 2A) were micrographed using a UV band pass filter cube, thereby showing the NAM stained cells. 2C) The same cells as 2A) were micrographed using a green long pass filter cube, thereby showing the PI stained cells. (40× magnification).
Figure 2:
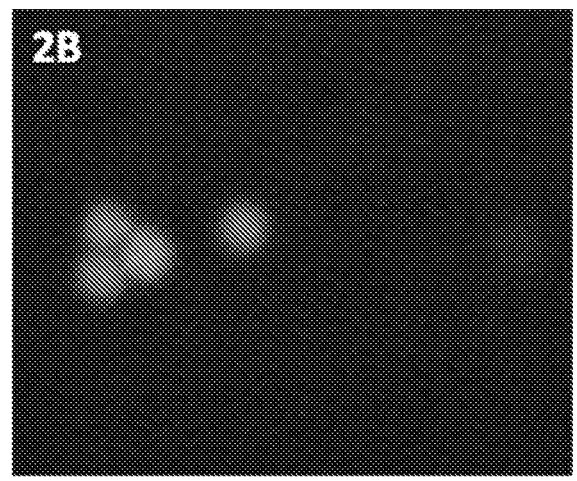
Figure 2:
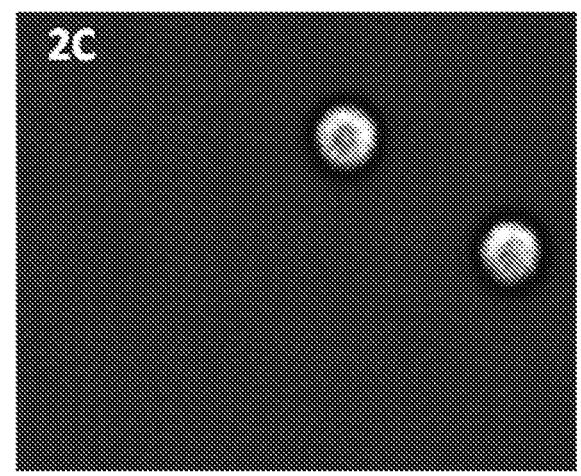

Results. As with the proliferating Jurkat cells, NAM and PI were found to complementary stain the outgrown HEK293 cells as revealed by fluorescence microscopy. (See 2A-2C in FIG. 2). Thus, NAM also functions to determine viability in stressed and outgrown cells. All Triton X-100 treated cells were PI positive and NAM negative, this suggests that an intact cell membrane is required for NAM staining.

Example 3

Use of NAM to determine viability of Drosophila S2 cells (Drosophila melanogaster Schneider line-2 (S2) cells were originally derived from late embryonic stage Drosophila embryos.)

Materials and Methods. Drosophila S2 cells were grown at 28° C. without shaking in Schneider's Drosophila medium (Invitrogen, #21720) supplemented with 10% heat-inactivated fetal bovine serum (Invitrogen, #10108-165). S2 cells (cell density $1.7 \times 10^7$, 99% viable determined using the YC-100 NucleoCounter system with diploid settings following the manufacturer's (ChemoMetec) protocol) were diluted 10 times in PBS and stained with 10 μg/mL NAM (Sigma, #01665). Cells were loaded into a NucleoCassette, containing the DNA stain propidium iodide (PI). The cells were investigated using an Olympus IX50 fluorescence microscope, and images were captured using a Lumenera CCD camera and in-house developed software. PI and NAM fluorescence were detected using, respectively, U-MWG2 (green long pass: 510-550 nm) and U-MNUA2 (UV band pass, 330-385 nm) filter cubes (Olympus).

Figure 3:
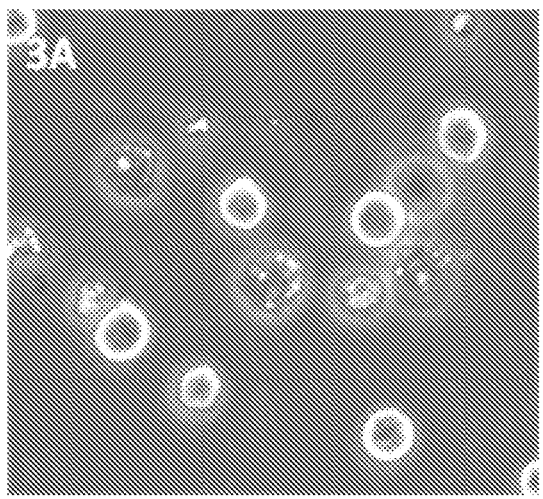
FIG. 3: 3A) Phase contrast image of S2 cells. 3B) The same cells as 3A) were micrographed using a UV band pass filter cube, thereby showing the NAM stained cells. 3C) The same cells as 3A) were micrographed using a green long pass filter cube, thereby showing the PI stained cells. (40× magnification).
Figure 3:
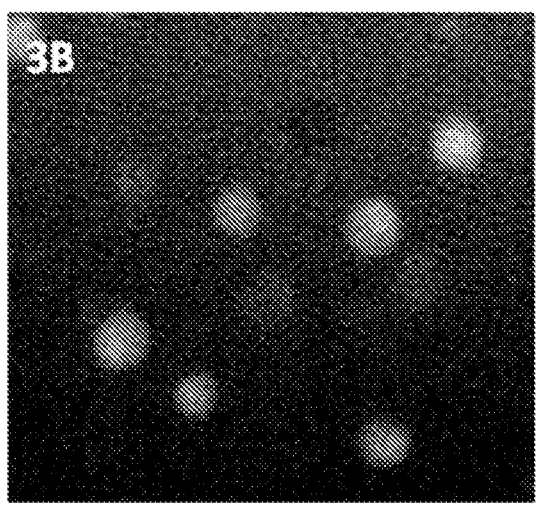
Figure 3:
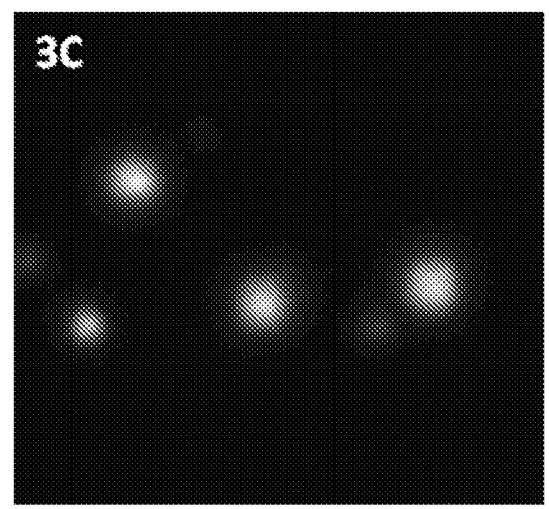

Results. As with the proliferating Jurkat cells and the outgrown HEK293 cells, NAM and PI were found to complementary stain S2 cells as revealed by fluorescence microscopy. (See 3A-3C in FIG. 3). Hence, NAM can also be used to measure viability in insect cells.

Example 4

The reaction of N-(9-acridinyl)maleimide (NAM) with —SH reagents

Materials and Methods. The excitation spectra of NAM, glutathione GSH, GSSG and 1,4-dithiothreitol (DTT) and combinations thereof were obtained using a spectroflourophotometer (RF-5301 Fluorescence Spectrophotometer, Shimadzu). 10 μL NAM dissolved in DMSO (100 μg/mL) were added to 3 mL distilled water (resulting concentration of NAM; 0,33 μg/mL) in a quartz cuvette and the excitation spectrum was recorded. Likewise were the spectra of NAM (0.33 μg/mL) together with GSH (167 μg/mL), NAM (0.33 μg/mL) together with GSSG (167 μg/mL), NAM together with DTT (167 μg/mL), GSH (167 μg/mL) alone, GSSG (167 μg/mL) alone and DTT (167 μg/mL) alone recorded.

Figure 4:
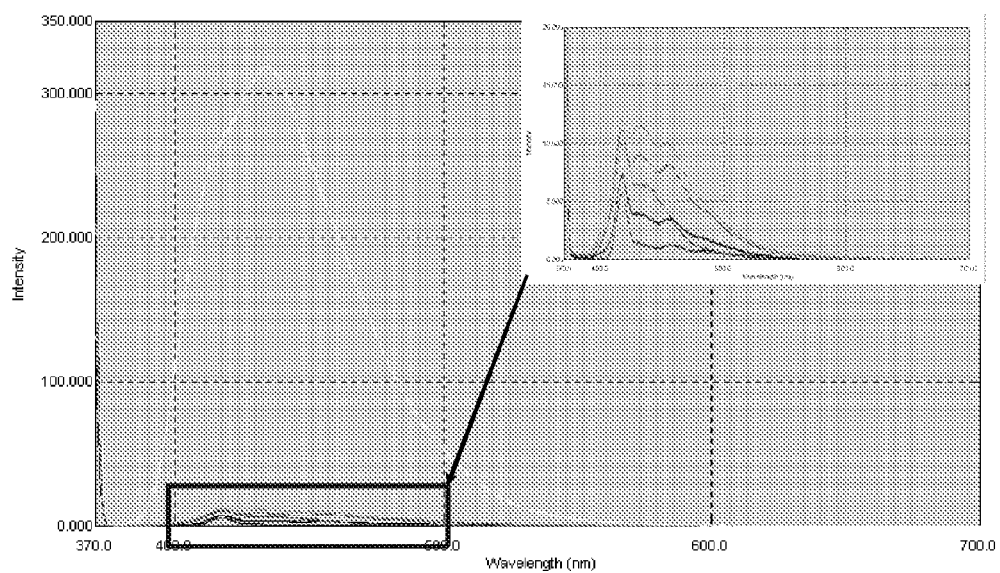
FIG. 4: Emission spectra. X axis; wavelength (nm), Y axis; relative intensity units. Black; water (background level), Blue; NAM, Red; reduced glutathione (GSH), Pink; oxidized glutathione (GSSG); Green; GSSG+NAM, yellow; NAM+GSH.
Figure 5:
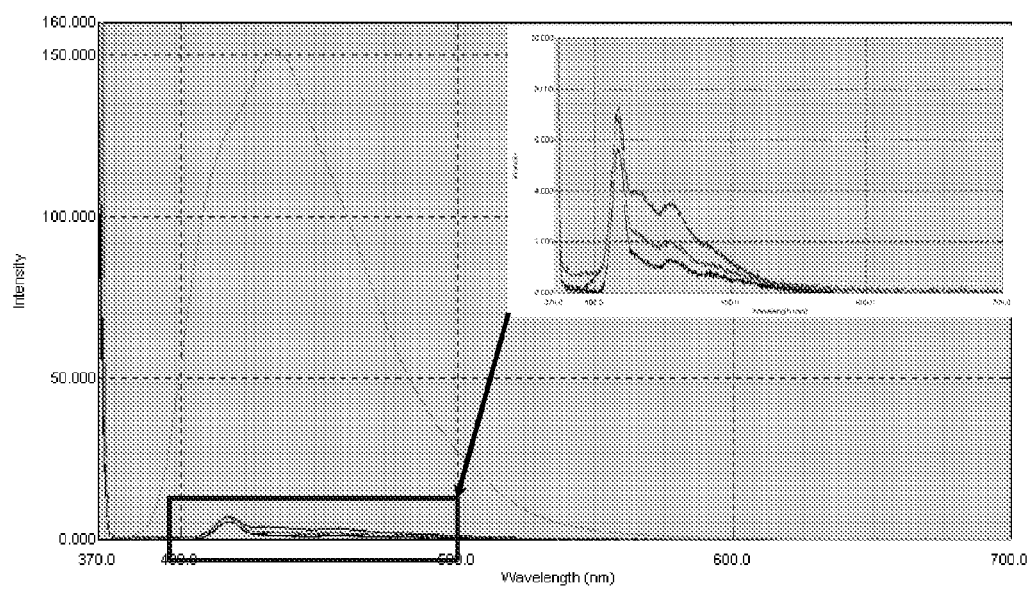
FIG. 5: Emission spectra. X axis; wavelength (nm), Y axis; relative intensity units. Excitation spectra. X axis; wavelength (nm), Y axis; relative intensity units. Black; water (background level), Blue; NAM, Red; DTT, green; DTT+NAM.

Results. NAM, glutathione (GSH and GSSG) and DTT alone only exhibited very weak fluorescence, however, mixing NAM with DTT or GSH, but not GSSG, gave a strong synergistic effect with respect to fluorescence. See FIG. 4 and FIG. 5. As NAM together with glutathione GSH and DTT exhibit much stronger fluorescence than the additive effect, this suggests that NAM reacts with glutathione (GSH) and DTT and forms a new fluorescent compound.

Example 5

Application of 7-diethylamino-3-[-(4'-maleimidylphenyl)]-4-methylcoumarin (CPM) as marker of cell viability Materials and Methods. Jurkat (JM) cells were grown at 37° C. in a humidified air atmosphere with 5% $CO_2$ in RPMI (Invitrogen, #61870) supplemented with 10% heat-inactivated fetal bovine serum (Invitrogen, #10108-165). 90 μL proliferating Jurkat cells (cell density $1.0 \times 10^6$, 99% viable determined using the NC-100 NucleoCounter system following the manufacturer's (ChemoMetec) protocol) were added 10 μL CPM (7-diethylamino-3-[4'-maleimidylphenyl]-4-methylcoumarin, Chemodex Ltd., CAS no. 76877-33-3) dissolved in DMSO (100 μg CPM pr. mL DMSO) and mixed by pipetting. Cells were loaded into a NucleoCassette, containing the DNA stain propidium iodide (PI). The cells were investigated using an Olympus IX50 fluorescence microscope, and images were captured using a Lumenera CCD camera and in-house developed software. PI and CPM fluorescence were detected using, respectively, U-MWG2 (green long pass: 510-550 nm) and U-MNUA2 (UV band pass, 330-385 nm) filter cubes (Olympus).

Figure 6:
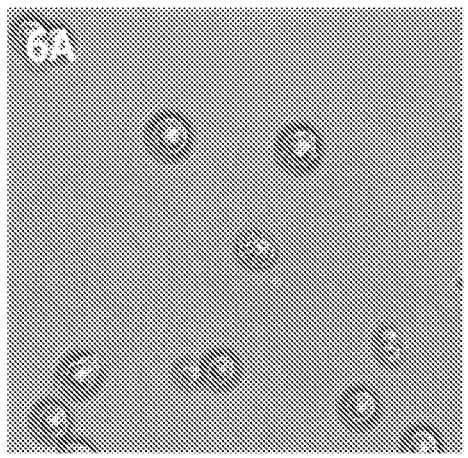
FIG. 6: 6A) Phase contrast image of Jurkat cells. 6B) The same cells as 6A) were micrographed using a UV band pass filter cube, thereby showing the CPM stained cells. 6C) The same cells as 6A) were micrographed using a green long pass filter cube, thereby showing the PI stained cells. (40× magnification).
Figure 6:
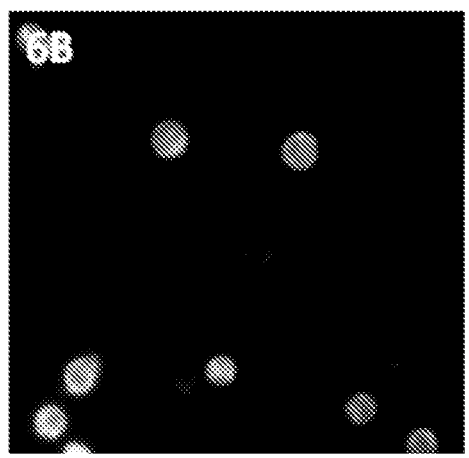
Figure 6:
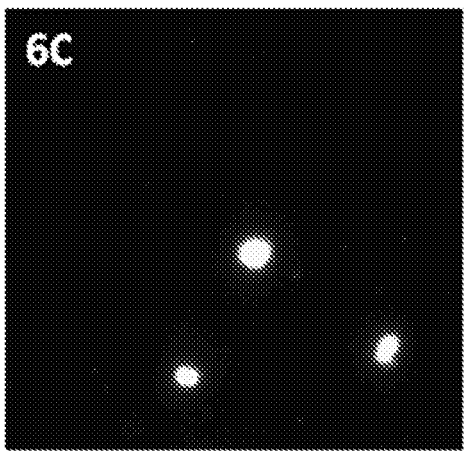

Results. Observing the CPM stained cells under a fluorescence microscope using a UV filter it was clear that nearly all cells were stained by CPM; and (as with NAM) only exception were PI positive cells (observed using the green long pass filter). (See 6A-6C in FIG. 6). Thus, also CPM can be used as a marker of cell viability.

Example 6

Reduced NAM localizes to the cytosol and nucleus

Materials and Methods. MCF-7 (ATTC HTB-22) and U2OS (ATTC HTB-96) cells were cultivated in RPMI (Invitrogen, #61870) +10% FCS (Invitrogen, #10108-165). Cells were transfected with, respectively, pEGFP-C1 (Clontech) and pBOS-H2B-GFP (Pharmingen, BD Biosciences) using Lipofectamine 2000 (Invitrogen, #11668-027) according to manufacturer's instructions. Stable cell lines expressing GFP (green fluorescent protein) or H2B-GFP (GFP N-terminally fused to histone H2B) were cultivated in, respectively, T25 flasks and in chamber slides (Nunc) to 75% confluency. Cells from T25 flasks were harvested with 0.5 ml of trypsin (Invitrogen, #25300), neutralized with 5 ml of medium (RPMI +10% FCS), stained with 10 pg/ml NAM (N-(9-acridinyl), maleimide, Sigma, #01665) prior to mounting on a microscope slide. Cells grown on chamber slides were directly stained with 10 μg/ml NAM (N-(9-acridinyl)-maleimide). Olympus IX50 was used for microscopy, and images were captured using a Lumenera CCD camera and in-house developed software. GFP and NAM fluorescence were detected using, respectively, U-MNIB3 and U-MNUA2 filter cubes (Olympus).

Results. Cells expressing GFP or H2B-GFP were used for determining the intracellular localization of fluorescent NAM. GFP localizes to the cytosol and nucleus (Seibel, N. M., Eljouni, J., Nalaskowski, M. M., and Hampe, W. Anal Biochem. 2007, 368:95-9.), whereas the H2B-GFP fusion protein exclusively localizes to chromatin and, hence, in the nucleus (Kanda, T., Sullivan, K. F., and Geoffrey, M. W. Curr. Biology. 1998, 8:377-385).

Fluorescence microscopy of GFP-expressing cell lines revealed that NAM and GFP co-localize completely, implying that NAM is found in both the nucleus and cytosol (FIGS.

Figure 7:
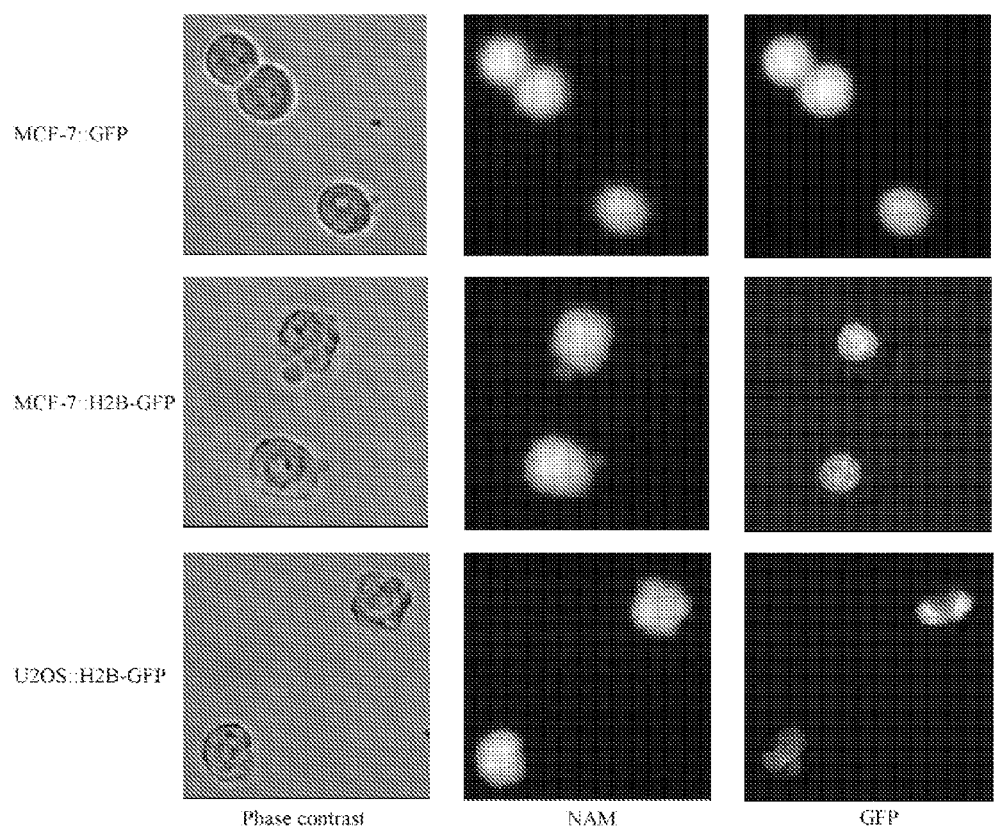
FIG. 7: Flourescence microscopy of GFP-expressing MCF-7 and U2OS cells grown in T25 flasks. Cells were de-attached from the flasks prior to NAM staining and micrographing (40× magnification). Each panel shows the following images of the same cells: left; phase contrast, centre; NAM, right; GFP.
Figure 8:
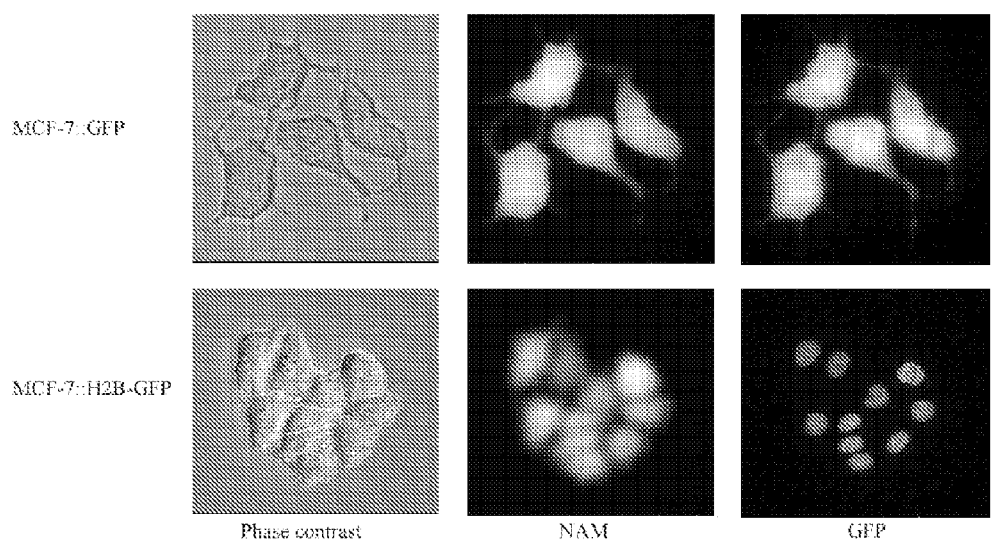
FIG. 8: Flourescence microscopy of GFP-expressing MCF-7 cells grown in chamber slides. Cells were NAM stained and micrographed (40× magnification). Each panel shows the following images of the same cells: left; phase contrast, centre; NAM, right; GFP.

7 and 8, upper panels). Supporting this notion microscopy of H2B-GFP-expressing cells showed that NAM and H2B-GFP only partial co-localize. NAM is found outside as well as inside the nucleus (FIG. 7 middle panel and FIG. 8 lower panel).

Example 7

Application of N-(1-Pyrenyl)maleimide (PM) as marker of cell viability

Materials and Methods. Jurkat (JM) cells were grown at 37° C. in a humidified air atmosphere with 5% $CO_2$ in RPMI (Invitrogen, #61870) supplemented with 10% heat-inactivated fetal bovine serum (Invitrogen, #10108-165). 90 µL proliferating Jurkat cells (cell density $1.1 \times 10^6$, 98% viable determined using the NC-100 NucleoCounter system following the manufacturer's (ChemoMetec) protocol) were added 10 µL PM (N-(1-Pyrenyl)maleimide, Sigma P7908 CAS no. 42189-56-0) dissolved in DMSO (100 µg PM pr. mL DMSO) and mixed by pipetting. Cells were loaded into a NucleoCassette, containing the DNA stain propidium iodide (PI). The cells were investigated using an Olympus IX50 fluorescence microscope, and images were captured using a Lumenera CCD camera and in-house developed software. PI and PM fluorescence were detected using, respectively, U-MWG2 (green long pass: 510-550 nm) and U-MNUA2 (UV band pass, 330-385 nm) filter cubes (Olympus).

Figure 9:
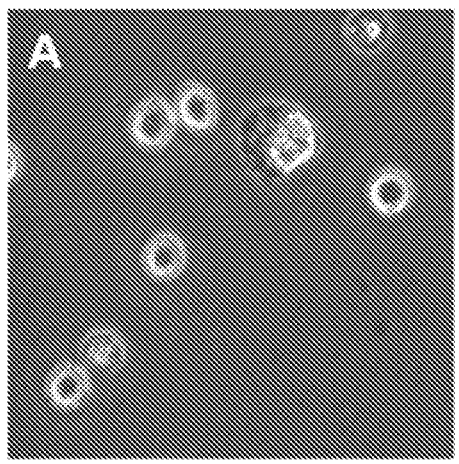
FIG. 9 A) Phase contrast image of proliferating Jurkat cells. B) The same cells as A) were micrographed using a UV band pass filter cube, thereby showing the PM stained cells. C) The same cells as A) were micrographed using a green long pass filter cube, thereby showing the PI stained cells (20× magnification).
Figure 9:
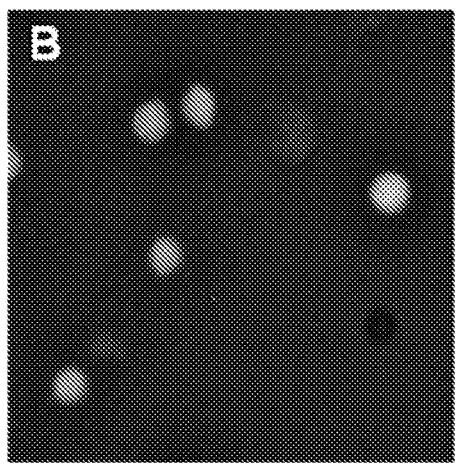
Figure 9:
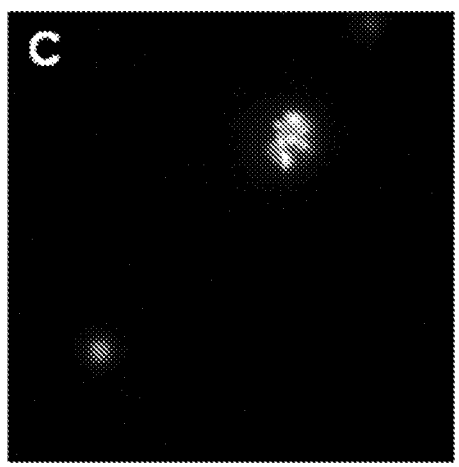

Results. Observing the PM stained cells under a fluorescence microscope using a UV filter it was clear that nearly all cells were stained by PM; and (as with NAM and CPM) only exception were PI positive cells (observed using the green long pass filter). (See A-C in FIG. 9). Thus, it appears that several substituted maleimides can be used to study cell viability.

Example 8

Use of NAM to determine viability of primary murine splenocytes

Materials and Methods. The spleen from a C57BL/6 mouse was placed in ice-cold PBS and gently ground using the end of a sterile syringe. The suspension was centrifuged at 300 g for 10 minutes; the pellet was resuspended in 1 mL 0.83% $NH_4Cl$ to lyse erythrocytes and incubated for 3 minutes on ice. The cells were then added 14 mL PBS and centrifuged at 300 g for 10 minutes. The splenocytes were resuspended in RPMI (Invitrogen, #61870) supplemented with 10% heat-inactivated fetal bovine serum (Invitrogen, #10108-165), 100 U/mL penicillin and 100 µg/mL streptomycin (Invitrogen, #15140-122). The cell clumps were allowed to sediment and were removed by pipetting, and the resulting single cell suspension was used. 90 µL splenocytes (cell density $1.7 \times 10^6$, 90% viable determined using the NC-100 NucleoCounter system following the manufacturer's (ChemoMetec A/S) protocol) were added 10 µL NAM (N-(9-acridinyl)maleimide, Sigma, #01665, CAS no. 49759-20-8) dissolved in DMSO (100 µg NAM pr. mL DMSO) and mixed by pipetting. Cells were loaded into a NucleoCassette, containing the DNA stain propidium iodide (PI). The cells were investigated using an Olympus IX50 fluorescence microscope, and images were captured using a Lumenera CCD camera and in-house developed software. PI and NAM fluorescence were detected using, respectively, U-MWG2 (green long pass: 510-550 nm) and U-MNUA2 (UV band pass, 330-385 nm) filter cubes (Olympus).

Figure 10:
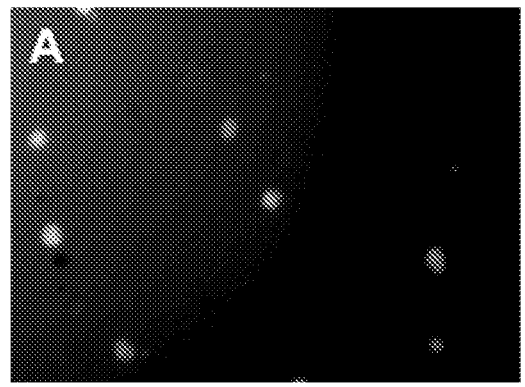
FIG. 10 A) Phase contrast image of primary murine splenocytes. B) The same cells as A) were micrographed using a UV band pass filter cube, thereby showing the NAM (4) stained cells. C) The same cells as A) were micrographed using a green long pass filter cube, thereby showing the PI stained cells (40× magnification).
Figure 10:
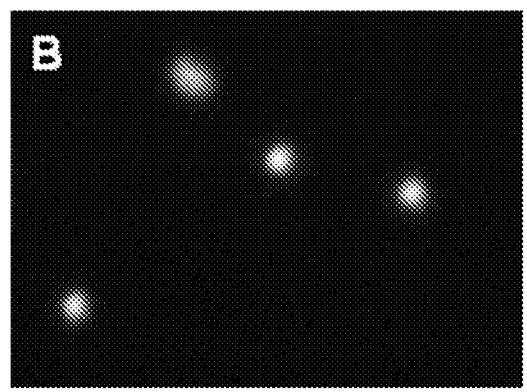
Figure 10:
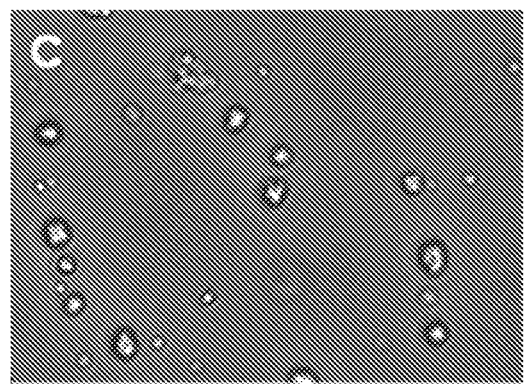

Results. Observing the NAM stained cells under a fluorescence microscope using a UV filter it was clear that nearly all the primary spleen cells were stained by NAM; only exception were PI positive cells (observed using the green long pass filter). (See A-C in FIG. 10). Thus, NAM also functions to determine viability in murine primary splenocytes.

Example 9

Use of NAM to determine viability of bone marrow derived cells

Materials and Methods. The bone marrow cells were harvested aseptically in the laminarflow hood. Briefly, bilateral tibia and femur were aseptically removed, freed of surrounding soft tissue, and placed in a petri dish with 10 mL 70% ethanol. After 2 minutes they were transferred to ice cold PBS. The bone marrow cavity was then flushed with 5 ml cold PBS using a 5-ml syringe with a 27-gauge needle attached, and the cells were collected from each bone. The cells were centrifuged at 300 g for 10 min, the supernatant was discarded, and cells were washed twice. After the second wash the cell pellet was resuspended in RPMI 1640 (Invitrogen, #61870) supplemented with 10% heat-inactivated fetal bovine serum (Invitrogen, #10108-165), 100 U/mL penicillin and 100 µg/mL streptomycin (Invitrogen, #15140-122). 90 µL bone marrow cellss (cell density $1.7 \times 10^6$, 93% viable determined using the NC-100 NucleoCounter system following the manufacturer's (ChemoMetec A/S) protocol) were added 10 µL NAM (N-(9-acridinyl)maleimide, Sigma, #01665, CAS no. 49759-20-8) dissolved in DMSO (100 µg NAM pr. mL DMSO) and mixed by pipetting. Cells were loaded into a NucleoCassette, containing the DNA stain propidium iodide (PI). The cells were investigated using an Olympus IX50 fluorescence microscope, and images were captured using a Lumenera CCD camera and in-house developed software. PI and NAM fluorescence were detected using, respectively, U-MWG2 (green long pass: 510-550 nm) and U-MNUA2 (UV band pass, 330-385 nm) filter cubes (Olympus).

Figure 11:
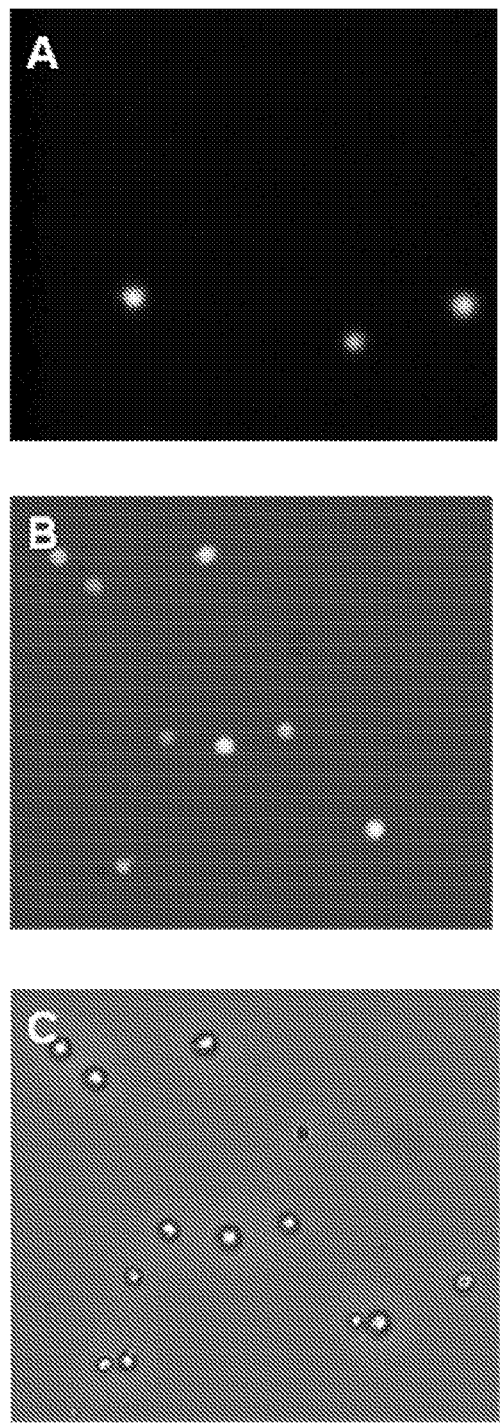
FIG. 11: A) Phase contrast image of murine bonemarrow cells. B) The same cells as A) were micrographed using a UV band pass filter cube, thereby showing the NAM (4) stained cells. C) The same cells as A) were micrographed using a green long pass filter cube, thereby showing the PI stained cells (40× magnification).

Results. Observing the NAM stained cells under a fluorescence microscope using a UV filter it was clear that nearly all the primary bone marrow cells were stained by NAM; again only exception were PI positive cells (observed using the green long pass filter). (See A-C in FIG. 11). Thus, NAM can also be used for to determining viability of bone marrow cells which consist of a mixture of various cell types such as fibroblasts, odioblasts, macrophages and stem cells.

Example 10

Haloacetamides: Application of 7-diethylamino-3-((4'-(iodoacetyl)amino)phenyl)-4-methylcoumarin (CPI) as marker of cell viability Materials and Methods. Jurkat (JM) cells were grown at 37° C. in a humidified air atmosphere with 5% $CO_2$ in RPMI (Invitrogen, #61870) supplemented with 10% heat-inactivated fetal bovine serum (Invitrogen, #10108-165). 90 µL proliferating Jurkat cells (cell density $1.1 \times 10^6$, 98% viable determined using the NC-100 NucleoCounter system following the manufacturer's (ChemoMetec) protocol) were added 10 µL CPI (7-diethylamino-3-((4'-(iodoacetyl)amino)phenyl)-4-methylcoumarin, Sigma 78264 CAS no. 76877-34-4) dissolved in DMSO (100 µg CPI pr. mL DMSO) and mixed by pipetting. Cells were loaded into a NucleoCassette, containing the DNA stain propidium iodide (PI). The cells were investigated using an Olympus IX50 fluorescence microscope, and images were captured using a Lumenera CCD camera and in-house developed software. PI and CPI fluorescence were detected using, respectively, U-MWG2 (green long pass: 510-550 nm) and U-MNUA2 (UV band pass, 330-385 nm) filter cubes (Olympus).

Figure 12:
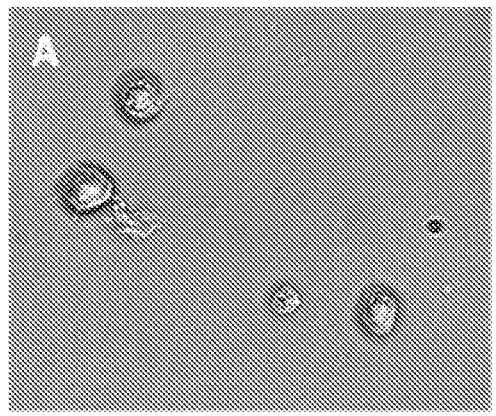
FIG. 12 A) Phase contrast image of proliferating Jurkat cells. B) The same cells as A) were micrographed using a UV band pass filter cube, thereby showing the CPI stained cells. C) The same cells as A) were micrographed using a green long pass filter cube, thereby showing the PI stained cells (20× magnification).
Figure 12:
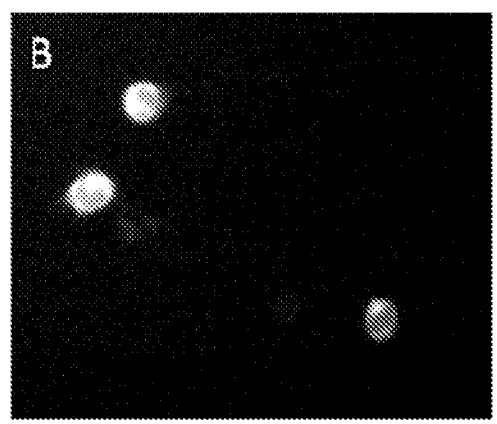
Figure 12:
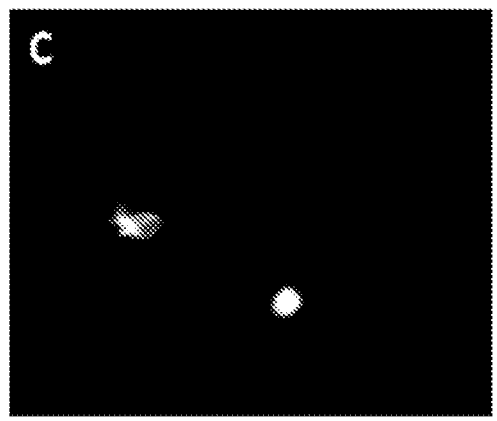

Results. Observing the CPI stained cells under a fluorescence microscope using a UV filter it was clear that nearly all cells were stained by CPI; and (as with the maleimides NAM, CPM and PM) only exception were PI positive cells (observed using the green long pass filter). (See A-C in FIG. 12). Thus, also fluorophore substituted/coupled iodoacetamides can be used to study cell viability.

Example 11

Application of N-(7-dimethylamino-4-methyl-3-coumarinyl)-maleimide (DACM) as marker of cell viability Materials and Methods. Jurkat (JM) cells were grown at 37° C. in a humidified air atmosphere with 5% $CO_2$ in RPMI (Invitrogen, #61870) supplemented with 10% heat-inactivated fetal bovine serum (Invitrogen, #10108-165). 90 µL proliferating Jurkat cells (cell density $0.9\times10^6$, 98% viable determined using the NC-100 NucleoCounter system following the manufacturer's (ChemoMetec) protocol) were added 10 µL DACM (N-(7-dimethylamino-4-methyl-3-coumarinyl)-maleimide, WAKO Pure Chemical Industries, CAS no. 55145-14-7) dissolved in DMSO (100 µg DACM pr. mL DMSO) and mixed by pipetting. Cells were loaded into a NucleoCassette, containing the DNA stain propidium iodide (PI). The cells were investigated using an Olympus IX50 fluorescence microscope, and images were captured using a Lumenera CCD camera and in-house developed software. PI and DACM fluorescence were detected using, respectively, U-MWG2 (green long pass: 510-550 nm) and U-MNUA2 (UV band pass, 330-385 nm) filter cubes (Olympus).

Figure 13:
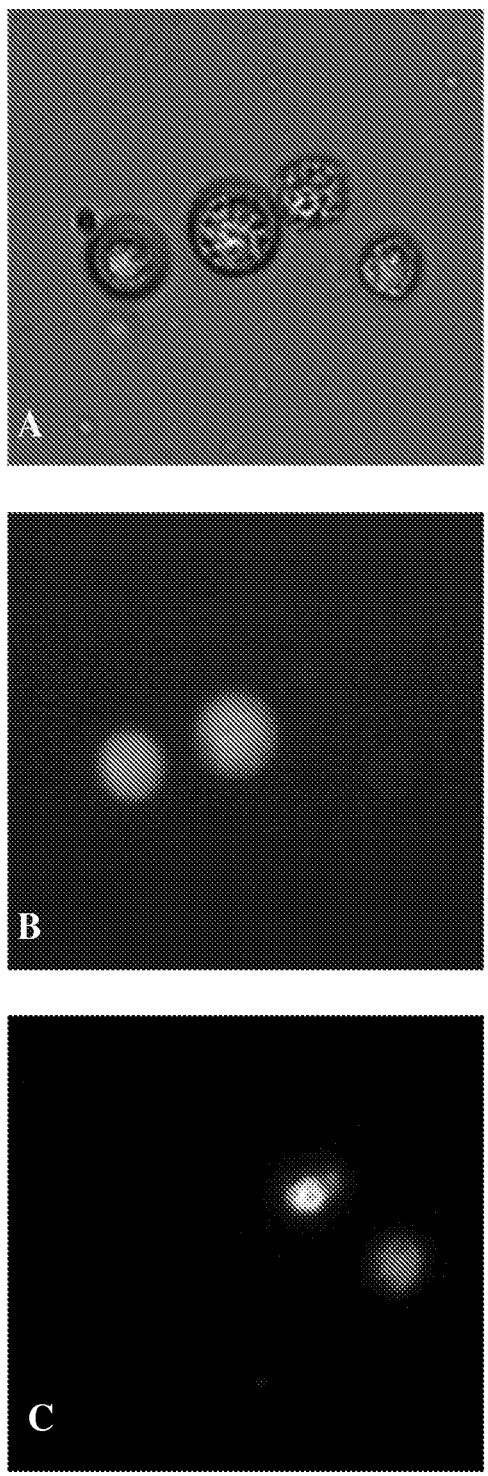
FIG. 13 A) Phase contrast image of proliferating Jurkat cells. B) The same cells as A) were micrographed using a UV band pass filter cube, thereby showing the DACM stained cells. C) The same cells as A) were micrographed using a green long pass filter cube, thereby showing the PI stained cells (20× magnification).

Results. Observing the DACM stained cells under a fluorescence microscope using a UV filter it was clear that nearly all cells were stained by DACM; and (as with the other maleimides NAM, CPM and PM) only exception were PI positive cells (observed using the green long pass filter). (See A-C in FIG. 13). Thus, it appears that also DACM can be used to study cell viability.

Example 12

Use of NAM to determine viability of bone marrow derived dendritic cells (BM-DCs)

Materials and Methods. Dendritic cells were developed from murine bone marrow derived cells as described by "Lutz, M. B., N. Kukutsch, A. L. Ogilvie, S. Rossner, F. Koch, N. Romani, and G. Schuler. 1999. An advanced culture method for generating large quantities of highly pure dendritic cells from mouse bone marrow. J Immunol Methods 223:77-92". Bone marrow cells were harvested aseptically in the laminar flow hood as described in example 11. Washed and resuspended bone marrow cells were resuspended in RPMI 1640 (Invitrogen, #61870) supplemented with 10% heat-inactivated fetal bovine serum (Invitrogen, #10108-165), 100 U/mL penicillin and 100 µg/mL streptomycin (Invitrogen, #15140-122). In addition, 15 ng/mL murine granulocyte-macrophage colony-stimulating factor (GM-CSF) was added and culture supernatant harvested from a GM-CSF-producing cell line (GM-CSF transfected Ag8.653 myeloma cell line. 0.7 mL of the cell suspension containing $3\times10^5$ leukocytes/mL was seeded into wells in a 12 well plate (Nunc, Germany) at day 0. An additional 0.7 mL fresh media (including 15 ng/mL GM-CSF) per well was added on day 3, and on day 6, 0.6 mL used media was replaced with 0.7 mL fresh media (including 15 ng/mL GM-CSF). On day 8, 0.7 mL of spent medium per well was replaced with 0.6 mL of media without GM-CSF and 1 µg/mL LPS (E. coli 026:B6; Sigma-Aldrich, # L2654) was added to induce maturation. The dendritic cell cultures were incubated for 15 h at 37° C. in 5% $CO_2$. Non-adherent cells were collected by gentle pipetting at the end of the incubation period and used for NAM staining. 90 µL dendritic cells (cell density $1.2\times10^6$, 97% viable determined using the NC-100 NucleoCounter system following the manufacturer's (ChemoMetec A/S) protocol) were added 10 µL NAM (N-(9-acridinyl)maleimide, Sigma, #01665, CAS no. 49759-20-8) dissolved in DMSO (100 µg NAM pr. mL DMSO) and mixed by pipetting. Cells were loaded into a NucleoCassette, containing the DNA stain propidium iodide (PI). The cells were investigated using an Olympus IX50 fluorescence microscope, and images were captured using a Lumenera CCD camera and in-house developed software. PI and NAM fluorescence were detected using, respectively, U-MWG2 (green long pass: 510-550 nm) and U-MNUA2 (UV band pass, 330-385 nm) filter cubes (Olympus).

Figure 14:
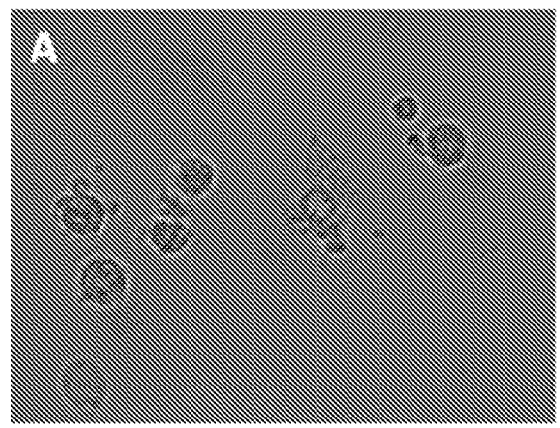
FIG. 14 A) Phase contrast image of murine dendritic cells. B) The same cells as A) were micrographed using a UV band pass filter cube, thereby showing the NAM dendritic cells. C) The same cells as A) were micrographed using a green long pass filter cube, thereby showing the PI stained cells (20× magnification).
Figure 14:
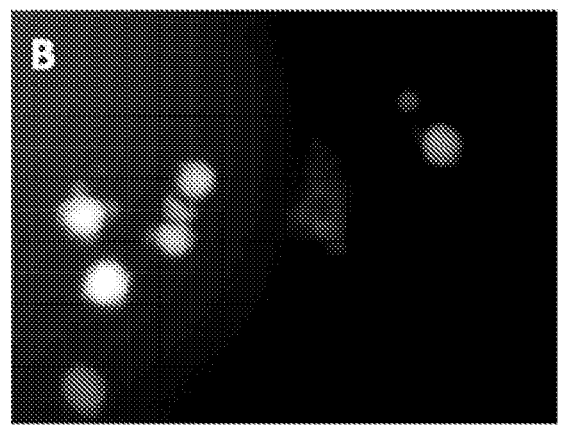
Figure 14:
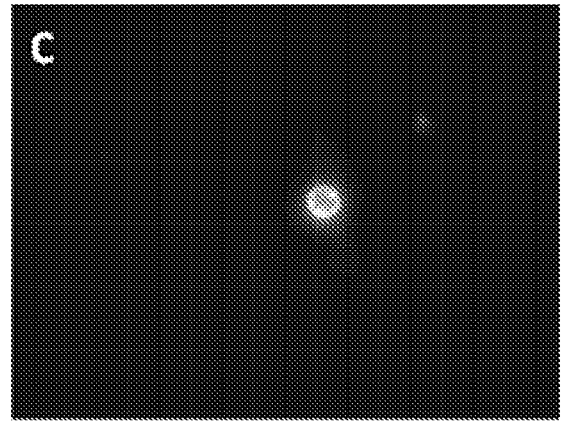

Results. Observing the NAM stained dendritic cells under a fluorescence microscope using a UV filter it was clear that nearly all the dendritic cells were stained by NAM; again only exception were PI positive cells (observed using the green long pass filter). (See A-C in FIG. 14). Thus, NAM can also be used for determining viability of primary dendritic.

Example 13

Bimanes: Application of monochlorobimane (mBC) as marker of cell viability

Materials and Methods. Dendritic cells were developed from murine bone marrow derived cells as described in example 14. 90 µL dendritic cellss (cell density $1.2\times10^6$, 97% viable determined using the NC-100 NucleoCounter system following the manufacturer's (ChemoMetec A/S) protocol) were added 10 µL mCB (monochlorobimane, Sigma, # 69899, CAS no. 76421-73-3) dissolved in DMSO (100 µg mCB pr. mL DMSO), mixed by pipetting and incubated at room temperature for 1 hour. Cells were loaded into a NucleoCassette, containing the DNA stain propidium iodide (PI). The cells were investigated using an Olympus IX50 fluorescence microscope, and images were captured using a Lumenera CCD camera and in-house developed software. PI and mCB fluorescence were detected using, respectively, U-MWG2 (green long pass: 510-550 nm) and U-MNUA2 (UV band pass, 330-385 nm) filter cubes (Olympus).

Figure 15:
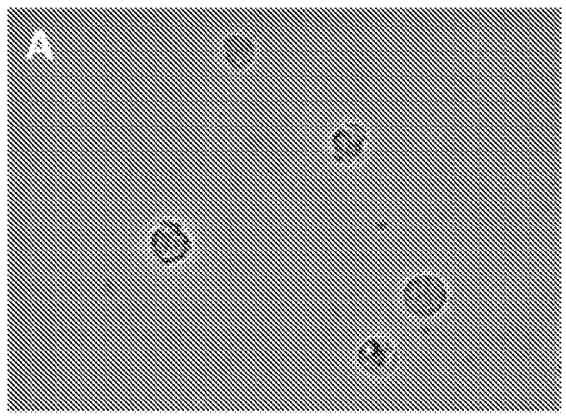
FIG. 15 A) Phase contrast image of murine dendritic cells. B) The same cells as A) were micrographed using a UV band pass filter cube, thereby showing the mCB stained cells. C) The same cells as A) were micrographed using a green long pass filter cube, thereby showing the PI stained cells (20× magnification).
Figure 15:
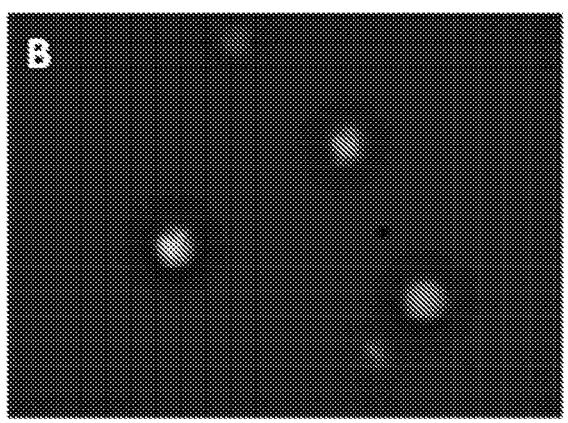
Figure 15:
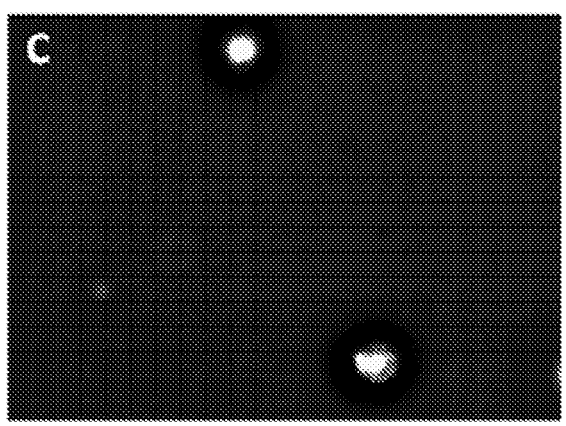

Results. Observing the mCB stained dendritic cells under a fluorescence microscope using a UV filter it was clear that nearly all the dendritic cells were stained by mCB; with the only exception being the PI positive cells (observed using the green long pass filter). (See A-C in FIG. 15). Thus, also mCB can also be used for determining viability of primary dendritic.

Example 14

The reaction of (N-(1-Pyrenyl)maleimide (PM) with oxidised and reduced glutathione Materials and Methods. The excitation spectra of PM, (N-(1-Pyrenyl)maleimide, glutathione GSH and GSSG and combinations thereof were obtained using a spectroflourophotometer (RF-5301 Fluorescence Spectrophotometer, Shimadzu). 10 µL PM dissolved in DMSO (100 µg/mL) were added to 3 mL distilled water (resulting concentration of PM; 0.33 µg/mL) in a quartz cuvette and the excitation spectrum was recorded. Likewise were the spectra of PM (0.33 µg/mL)

together with GSH (167 µg/mL), PM (0.33 µg/mL) together with GSSG (167 µg/mL), GSH (167 µg/mL) alone and GSSG (167 µg/mL) alone recorded.

Figure 16:
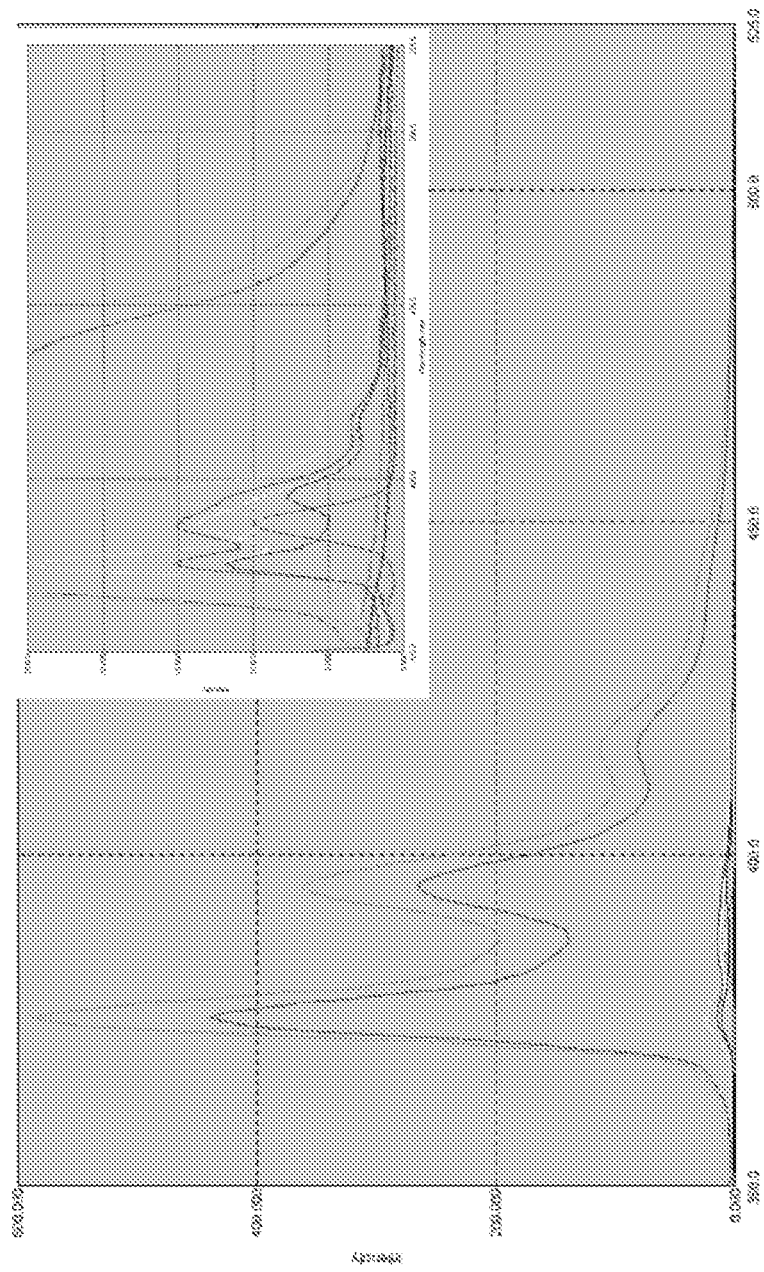
FIG. 16 PM spectra: Emission spectra. X axis; wavelength (nm), Y axis; relative intensity units. Black; GSH (excitation wavelength 275 nm). Blue; GSH (excitation wavelength 342 nm). Red; GSH+PM (excitation wavelength 275 nm), Green; GSH+PM (excitation wavelength 342 nm). Pink; GSSG (excitation wavelength 275 nm). Cyan; GSSG (excitation wavelength 342 nm). Yellow; GSSG+PM (excitation wavelength 275 nm). White, GSSG+PM (excitation wavelength 275 nm). Dark blue; PM (excitation wavelength 275 nm). Brown; PM (excitation wavelength 342).
Figure 17:
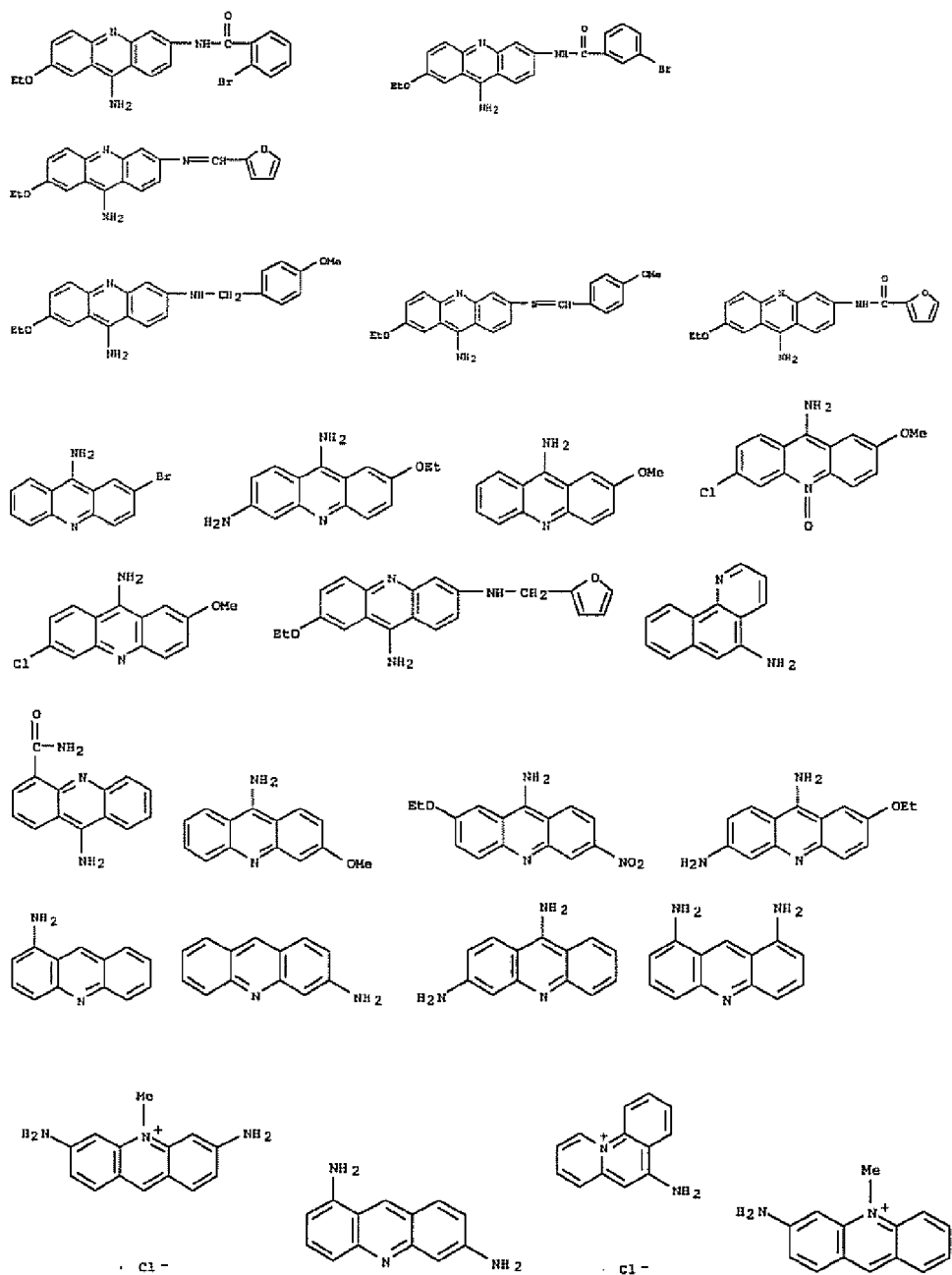
FIG. 17A-C Examples of known analogs or derivatives of 9-aminoacridine REPORTER type compounds which upon transformation of an amino group to a maleimide group is useful as CC-REPORTER type of compounds.
Figure 17:
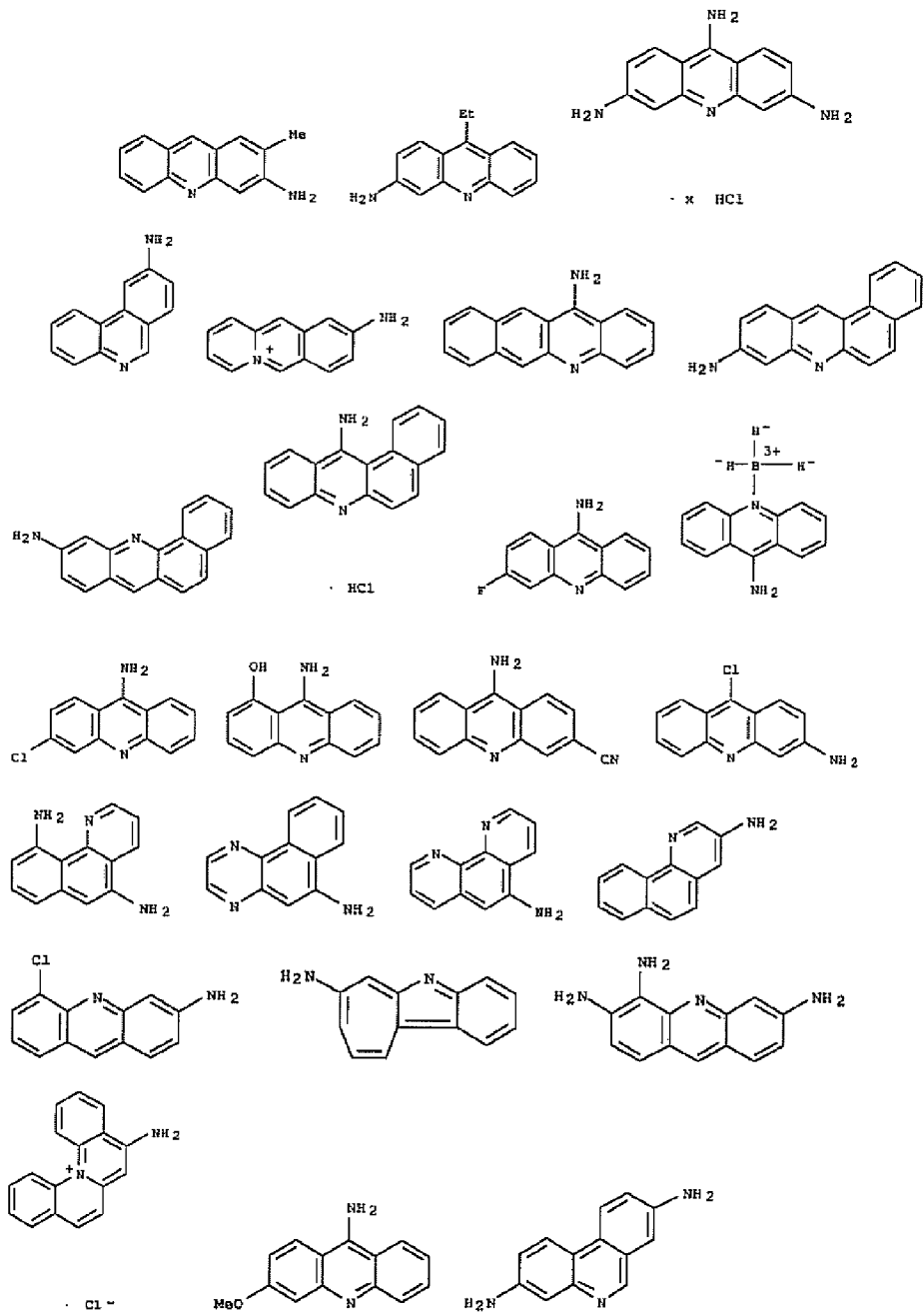
Figure 17:
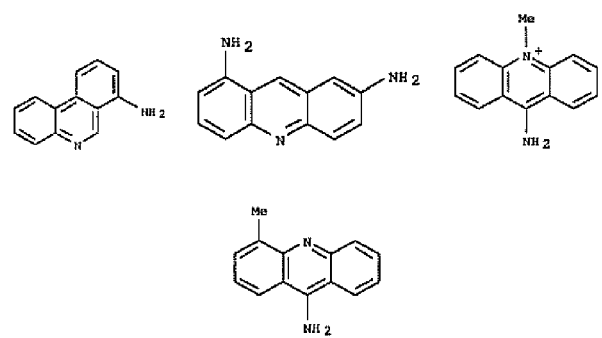
Figure 18:
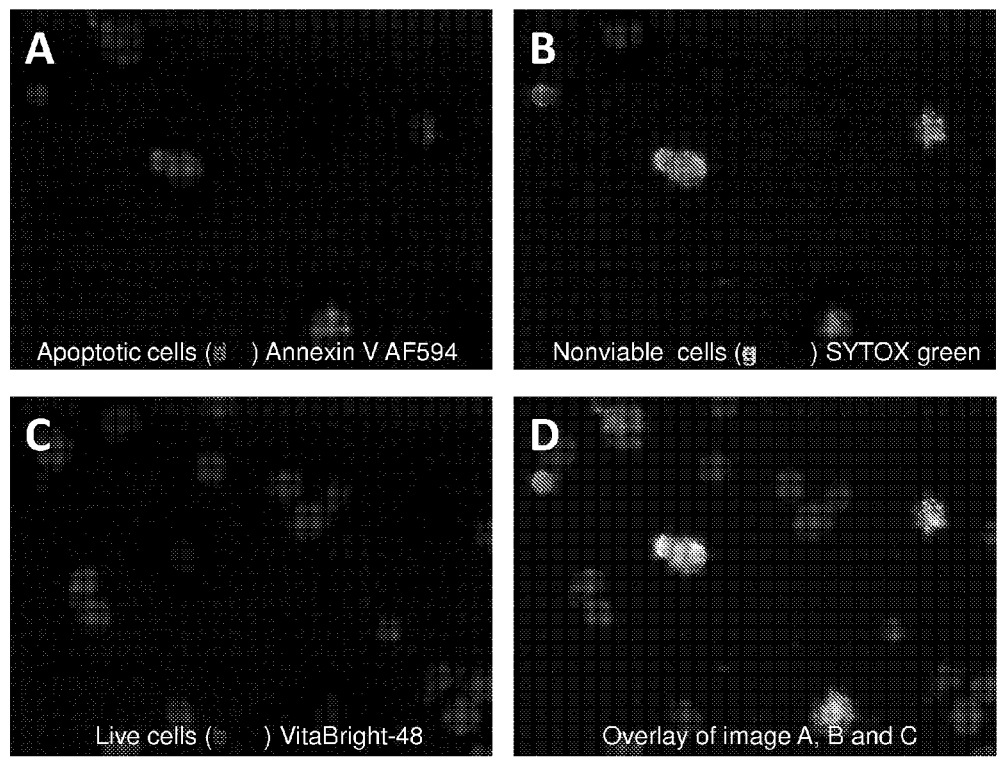
FIG. 18: Jurkat cells treated with the apoptosis-inducing drug nocodazole were triple-stained with the red fluorescent annexin V AF594 conjugate which stains apoptotic cells along with the green fluorescent nonviable stain SYTOX green and the violet fluorescent stain DACM. 18A) Annexin V positive cells were micrographed using a green long pass filter cube capable of detecting the red fluorescence of the Alexa Fluor 594 annexin V conjugate. 18B) The same cells as 18A) were micrographed using a blue band pass filter cube, thereby showing the SYTOX green fluorescence of all nonviable cells. 18C) The same cells as 18A) were micrographed using a UV band pass filter cube, thereby showing the DACM fluorescence of all cells. D) Overlay of image 18A), 18B) and 18C). Colour code; Red=annexin V AF594 (apoptotic cells); Green=SYTOX green (nonviable cells) and Blue=DACM (all viable cells—intensity depends on redox status of the cell). 40× magnification.
Figure 19:
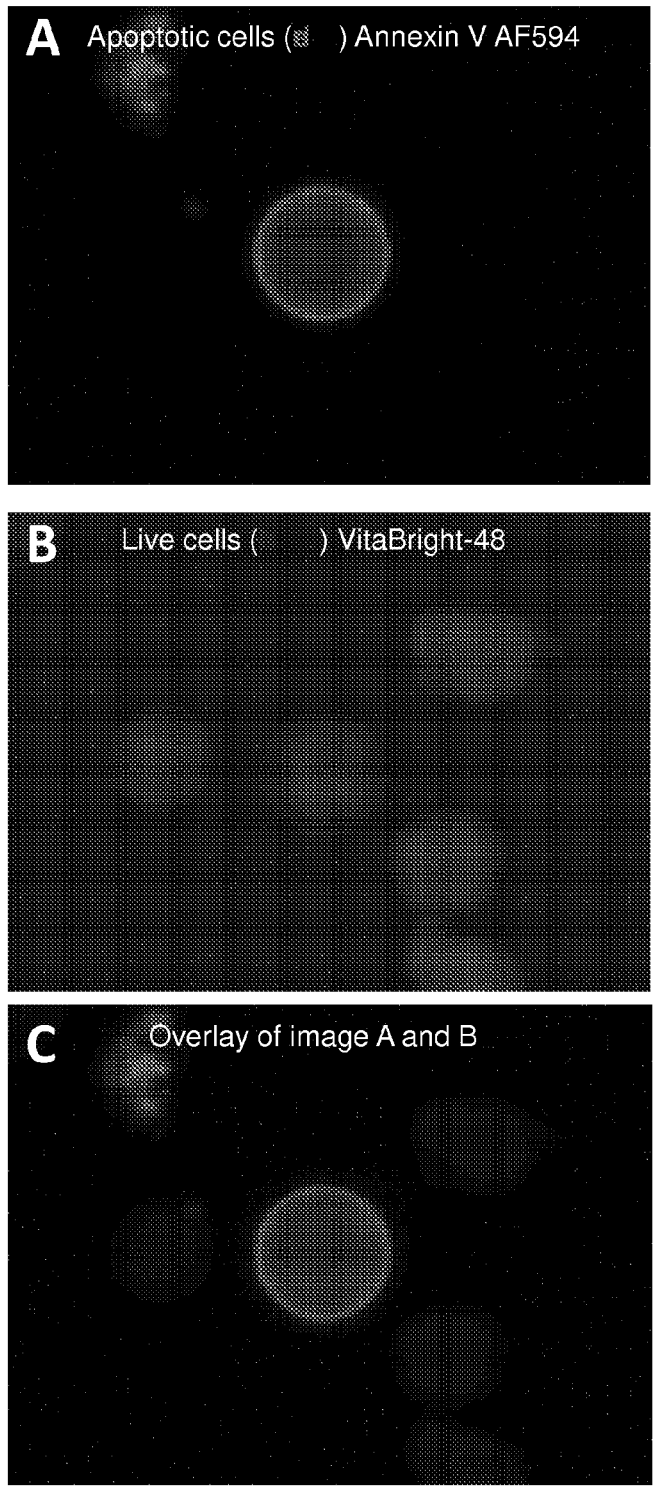
FIG. 19 Nocodazole treated Jurkat cells stained with the red fluorescent annexin V Alexa Fluor 594 conjugate, the nonviable stain SYTOX green and DACM. 19A) Annexin V positive cells were micrographed using a green long pass filter cube capable of detecting the red fluorescence of the annexin Alexa Fluor 594 conjugate. 19B) The same cells as 19A) were micrographed using a UV band pass filter cube, thereby showing the DACM fluorescence of all cells. 19C) Overlay of image 19A) and 19B). Colour code; Red=annexin V AF594; Green=SYTOX green (not visible as all cells in the image were viable) and Blue=DACM. 40× magnification.
Figure 20:
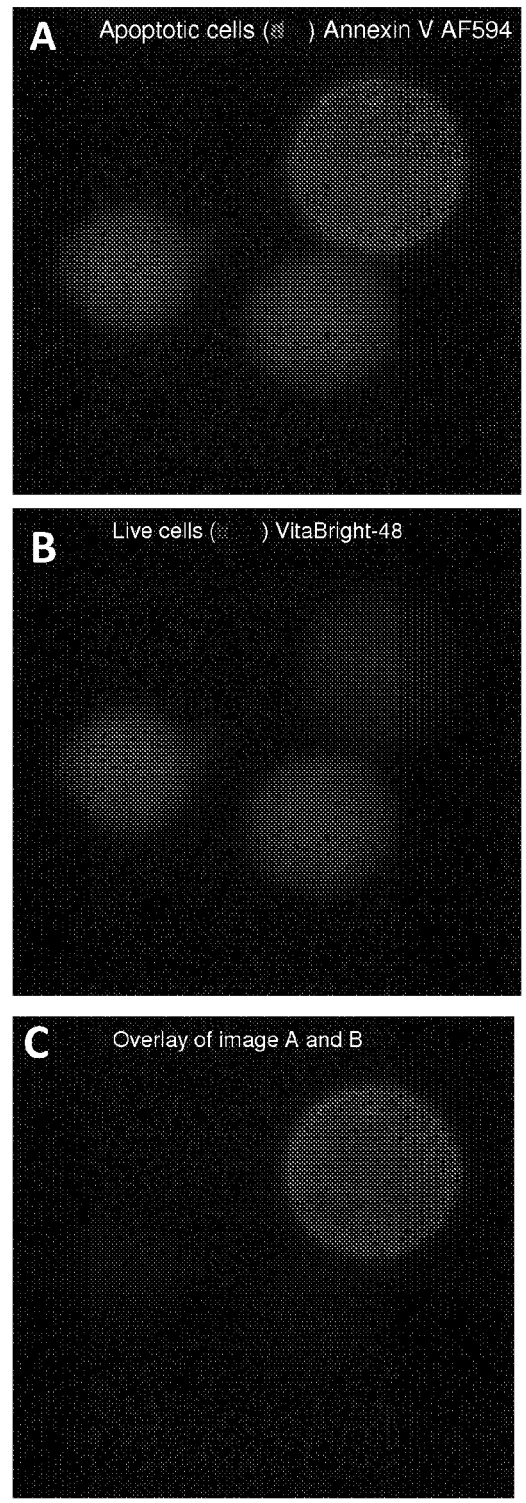
FIG. 20 Nocodazole treated Jurkat cells were stained with the red fluorescent annexin V Alexa Fluor 594 conjugate, the nonviable stain SYTOX green and DACM. 20A) Annexin V positive cells were micrographed using a green long pass filter cube capable of detecting the red fluorescence of the annexin V Alexa Fluor 594 conjugate. 2B) The same cells as 20A) were micrographed using a UV band pass filter cube, thereby showing the DACM fluorescence of all cells. 20C) Overlay of image 20A) and 20B). Colour code; Red=annexin V AF594 ; Green=SYTOX green (not visible as all cells in the image were viable) and Blue=DACM. 40× magnification.
Figure 21:
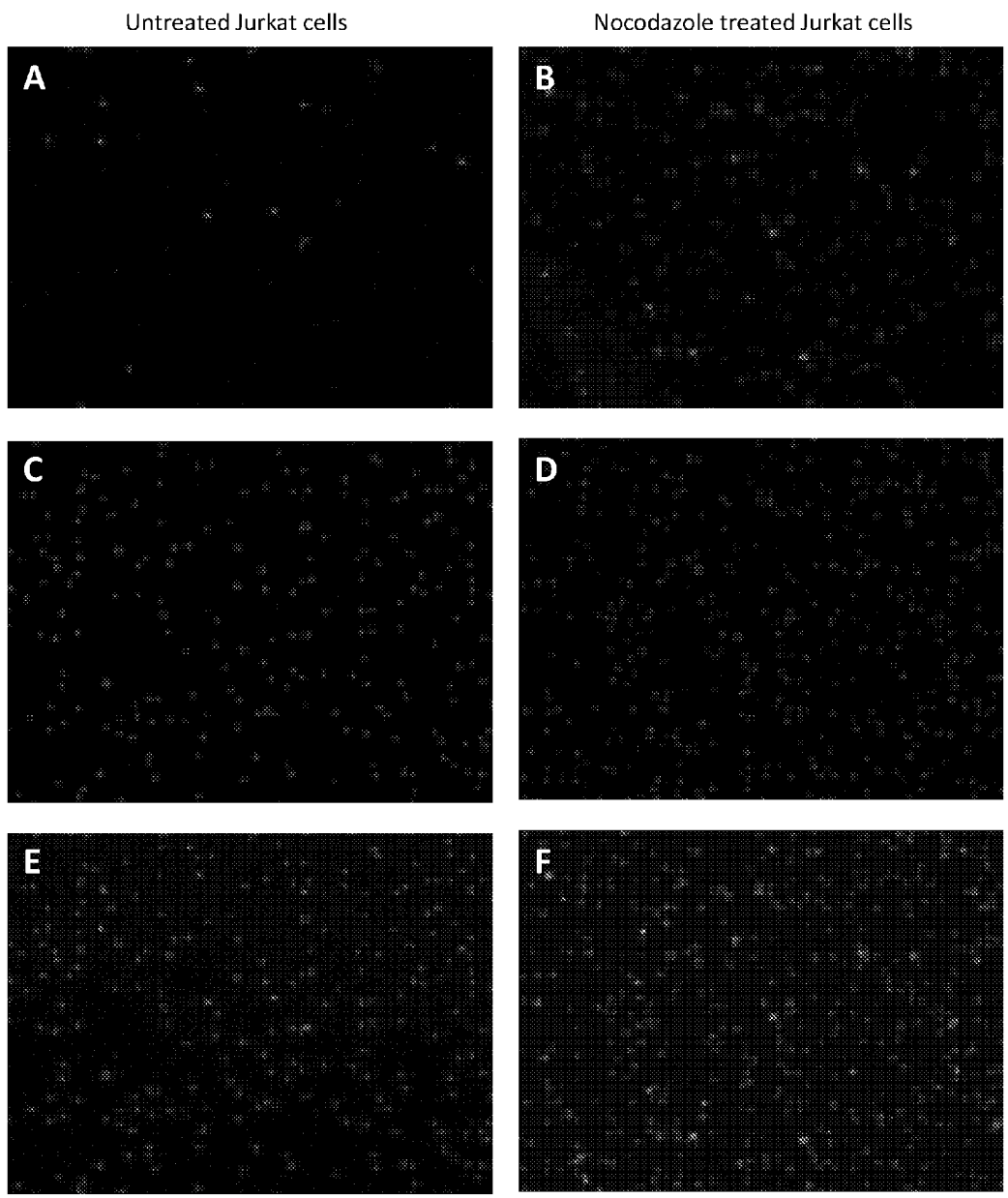
FIG. 21 Untreated Jurkat cells (left images), and nocodazole treated Jurkat cells (images to the right) were stained with the green nonviable stain SYTOX green, the red fluorescent annexin V Alexa Fluor 594 conjugate and DACM. 21A+21B) Annexin V positive cells were micrographed using a filter set capable of detecting the red fluorescence of the Alexa Fluor 594 annexin V conjugate. 21C+21D) The same cells as 21A+21B) were micrographed using a filter set capable of detecting UV thereby showing the DACM fluorescence of all cells. 21E+21F) Overlay of SYTOX green stained nonviable cells, annexin V Alexa Fluor 594 conjugate positive cells and DACM stained cells. As it appears from these images, the DACM fluorescence intensity depends on the cell viability; nonviable cells (identified as SYTOX green positive cells) exhibit a low fluorescence intensity and so does the apoptotic cells (annexin V positive cells). The viable, non-apoptotic cells exhibit the highest fluorescence intensity. Also refer to the following figure which shows the fluorescence intensity histogram of the DACM stained untreated and nocodazole treated cells. Colour code; Green=SYTOX green, Red=annexin V AF594 and Blue=DACM. 2× magnification.

Results. PM and glutathione (GSH and GSSG) only exhibited very weak fluorescence, however, mixing PM with GSH, but not GSSG, gave a strong synergistic effect with respect to fluorescence. See FIG. 16. As PM together with reduced glutathione (GSH) exhibit much stronger fluorescence than the additive effect, this suggests that PM reacts with glutathione (GSH) and forms a new fluorescent compound.

Example 15

Application of N-(7-dimethylamino-4-methyl-3-coumarinyl)-maleimide (DACM) for detection of apoptosis Materials and Methods. Jurkat (A3) cells were grown in T flasks at 37° C. in a humidified air atmosphere with 5% $CO_2$ in RPMI (Invitrogen, #61870) supplemented with 10% heat-inactivated fetal bovine serum (Invitrogen, #10108-165). In order of investigating the effect of an apoptosis-inducing drug on DACM staining, Jurkat cells were treated with nocodazole (0.5 µM) for 16 hours. Nocodazole treated and untreated control cells were harvested washed and stained with annexin V Alexa Fluor 594 (Invitrogen, #A13203) according to manufacturer's instructions. Then cells were stained with DACM (20 µg/mL) (N-(7-dimethylamino-4-methyl-3-coumarinyl)-maleimide, WAKO Pure Chemical Industries, CAS no. 55145-14-7) and the nonviable stain SYTOX green (0.3 µM) (Invitrogen, #S7020). Immediately after staining with DACM cells were loaded into a chamber slide. The cells were investigated using an Olympus IX50 fluorescence microscope, and images (40× magnification) of the Annexin V Alexa Fluor 594, DACM and SYTOX green stained cells were captured using a Lumenera CCD camera combined with the following filter cubes (Olympus); U-MWG2 (green long pass: 510-550 nm), U-MNUA2 (UV band pass, 330-385 nm) and U-MNIB3 (blue band pass: 470-495 nm). Cells were also investigated using an in-house developed fluorescence microscope system with 2× magnification.

Figure 22:
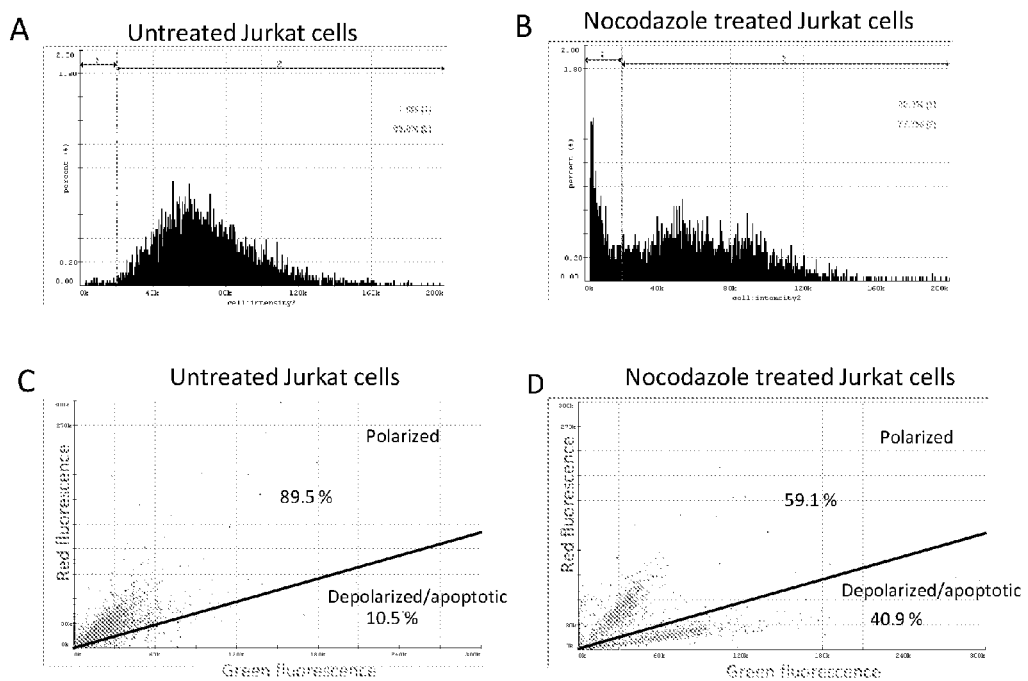
FIG. 22 The effect of the apoptotic drug nocodazole on the fluorescence intensity of stained Jurkat cells. 22A+22B) Fluorescence intensity of DACM stained untreated (22A) or nocodazole treated (22B) Jurkat cells. As seen from the histograms, the fluorescence intensity of the DACM stained cells decrease after nocodazole treatment. 22C+22D) Red vs. green fluorescence of JC-1 stained untreated (22C) and nocodazole treated (22D) Jurkat cells. The JC-1 stain is used for detecting apoptosis. JC-1 form red fluorescing aggregates in the mitochondria of healthy, non-apoptotic cells. In apoptotic cells JC-1 appears in its green monomeric, reduced form. Thus, mitochondrial depolarization due to apoptosis is revealed as a decrease in the red/green fluorescence intensity ratio. Treatment with nocodazole induces apoptosis (measured as depolarisation) in a cell subpopulation (22D). This is in accordance with the results obtained using DACM to measure the thiol level; treatment with nocodazole causes a decrease in the fluorescence intensity of a subpopulation of cells.

Results. We found that DACM can be used for investigating apoptosis and cell health by determining the level of free thiols such as reduced glutathione. A decrease in cellular GSH concentration is an early hallmark in the progression of cell death in response to different apoptotic stimuli. As DACM reacts with free thiols and forms a fluorescent product, measurement of the level of cellular thiols can be performed by quantifying cellular fluorescence. This information can then be used to determine cell health and apoptotic status. This is demonstrated here: As seen from FIG. 18-22, the DACM fluorescence intensity depends on the cell viability; nonviable cells (identified as SYTOX green positive cells) exhibit a low fluorescence intensity and so does the apoptotic cells with phosphatidyl-serine flipped to the outside of the plasma-membrane (annexin V positive cells). The viable, non-apoptotic cells exhibit the highest fluorescence intensity. As shown in FIG. 22, the overall fluorescence intensity of nocodazole treated Jurkat cells are lower than the overall fluorescence intensity of untreated Jurkat cells, correlating well with the results obtained using the JC-1 mitochondrial potential detection apoptosis assay.

Example 16

Application of N-(7-dimethylamino-4-methyl-3-coumarinyl)-maleimide (DACM) for monitoring of cell health Materials and Methods. Jurkat (A3) cells were grown in T flasks at 37° C. in a humidified air atmosphere with 5% $CO_2$ in RPMI (Invitrogen, #61870) supplemented with 10% heat-inactivated fetal bovine serum (Invitrogen, #10108-165). To investigate the effect of cell starvation on DACM staining, exponentially proliferating cells from a newly split culture (2 days incubation) were investigated along with cells from a stationary culture (10 days incubation). 1.8 mL proliferating newly split Jurkat cells (cell density $3 \times 10^5$, 98% viable) were spun down and resuspended in 95 µL RPMI media and added 5 µL of a mixture of DACM (N-(7-dimethylamino-4-methyl-3-coumarinyl)-maleimide, WAKO Pure Chemical Industries, CAS no. 55145-14-7, 400 µg DACM pr. mL), acridine orange (1.2 µg/mL) and propidium iodide (500 µg/mL) and mixed by pipetting. Immediately after staining cells were loaded into a chamber slide. Images were captured using an in-house developed fluorescence microscope system with a Lumenera CCD camera (2× magnification) and were analysed using in-house developed software.

Figure 23:
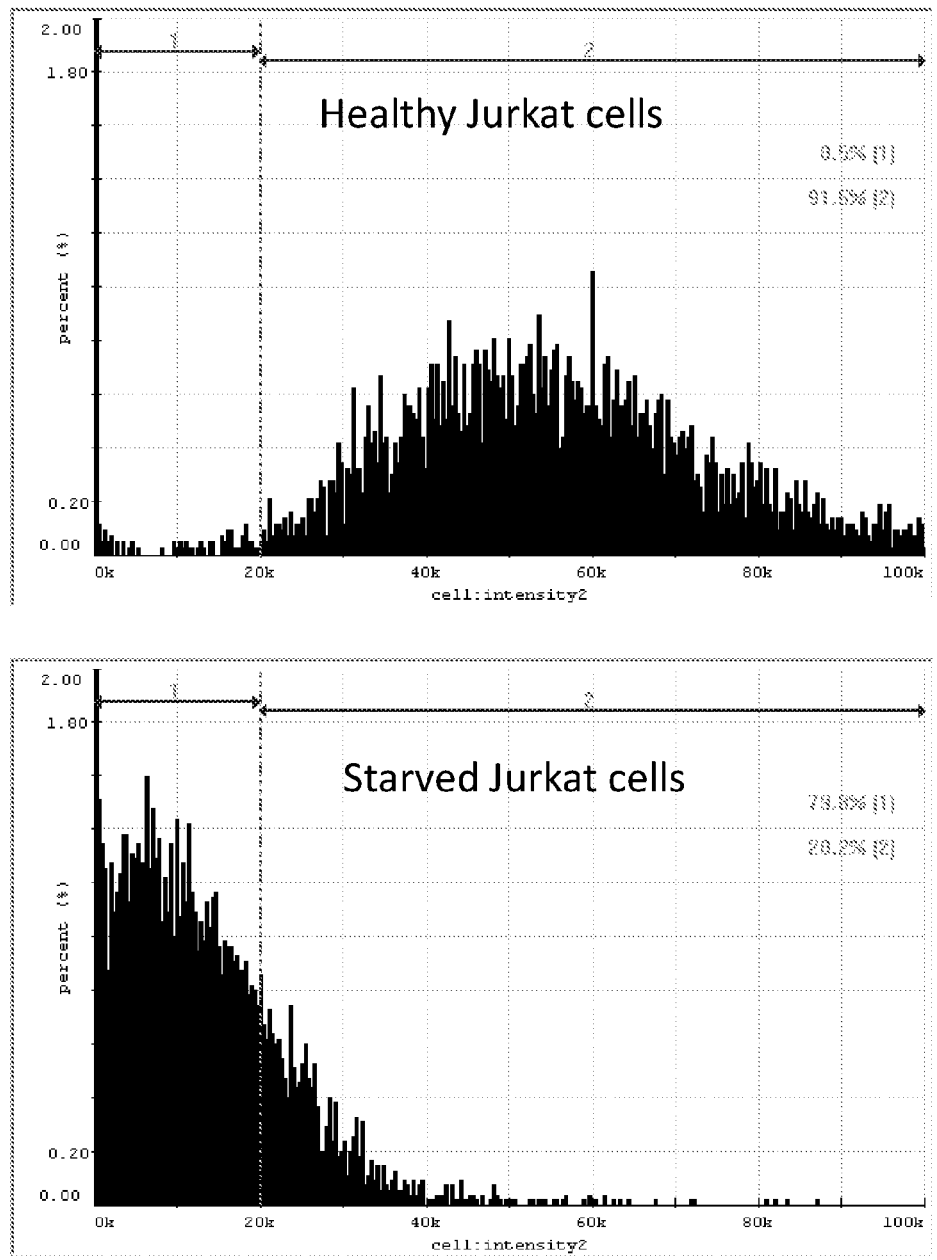
FIG. 23. Fluorescence intensity histogram of viable Jurkat cells stained with DACM. Cells were stained with DACM and PI, and nonviable cells were gated out based on PI uptake. As seen from the histogram is the fluorescence intensity higher for healthy (exponential growing) Jurkat cells than the starved Jurkat cells, demonstrating that DACM can be used as a measure of cell health.

Results. DACM can be used to detect changes in the intracellular level of (reduced) thiols. Such changes may occur in apoptotic cells or cells undergoing other pathological processes. As the intracellular reducing power available to the cell is an indicator of the overall health status, DACM can be used for monitoring cell health. As it is seen from the histograms (FIG. 23) the fluorescence intensity is higher for healthy (exponential growing) Jurkat cells than the starved Jurkat cells, thereby demonstrating the potential of using DACM for health checking a cell population.

Example 17

The use of DACM for rapid analysis of yeast viability

Materials and Methods. *S. pombe* strain Eg328, h$^{90}$ smt-0 ura4-D18, (ATCC 90720; Styrkarsdottir U et al. Curr. Genet. 23: 184-186, 1993) was grown in a rotary shaker at 29° C. to a density of $1 \times 10^7$ cells/ml in EMM minimal medium (Moreno et al., Methods Enzym. 194: 795-823, 1991) supplemented with 10 mM of L-uridine (Sigma, U3750). *S. cerevisiae* wild strain was cultivated in YPD medium (Qbiogene, #4001-032) at 29° C. to a density of $5 \times 10^7$ cells/ml. *S. pombe* and *S. cerevisiae* cells were directly stained with 8 µg/ml DACM (N-(7-dimethylamino-4-methyl-3-coumarinyl)-maleimide, WAKO Pure Chemical Industries, CAS no. 55145-14-7 dissolved in DMSO) and 10 µg/ml propidium iodide (Applichem, #A2261.9010) prior to mounting on a microscope slide. Note: after addition of DACM and PI the cells were immediately analysed for fluorescence (no incubation). Olympus IX50 and NucleoCounter® NC3000™ was used for microscopy, and images were captured using a Lumenera CCD camera and in-house developed software. Propidium iodide and DCAM fluorescence were detected using the U-MWG2 and U-MNUA2 filter cubes of the Olympus microscope and filterset 5 and 1 of the NucleoCounter® NC-3000™.

Figure 24:
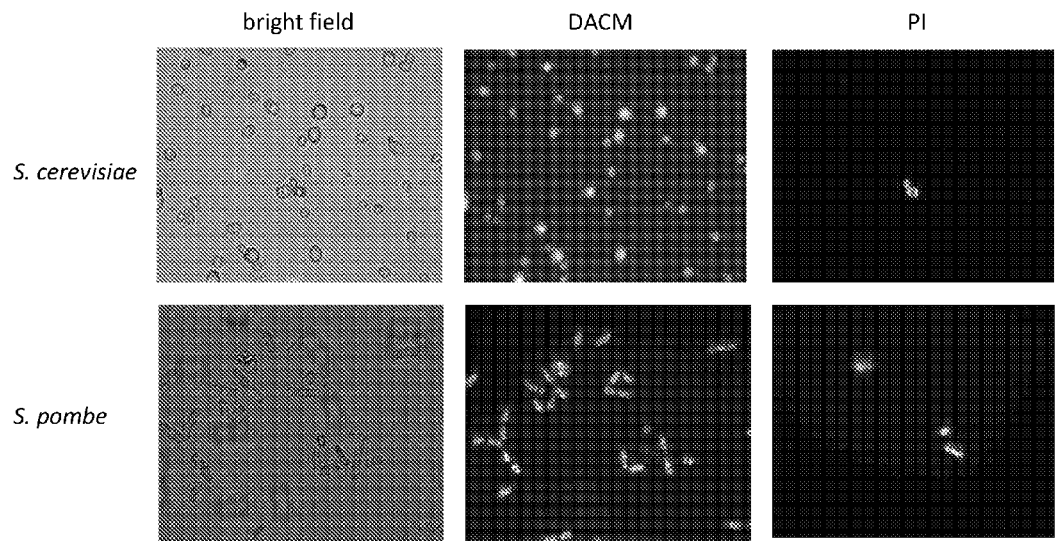
FIG. 24 Fluorescent microscopy of fission yeast (*S. pombe*) and budding yeast (*S. cerevisiae*) stained with DACM and propidium iodide and micrographed using (A) an Olympus IX50 microscope (40× magnification) or (B) Nucleo-Counter® NC-3000™ (2X magnification). (A) Each panel shows the following images of the same cells: left; bright field, middle; DACM, right; propidium iodide (PI). (B) Panel shows the following images of the same cells: Left; DACM, middle; propidium iodide (PI), Right; superimposition of DACM and PI images.
Figure 24:
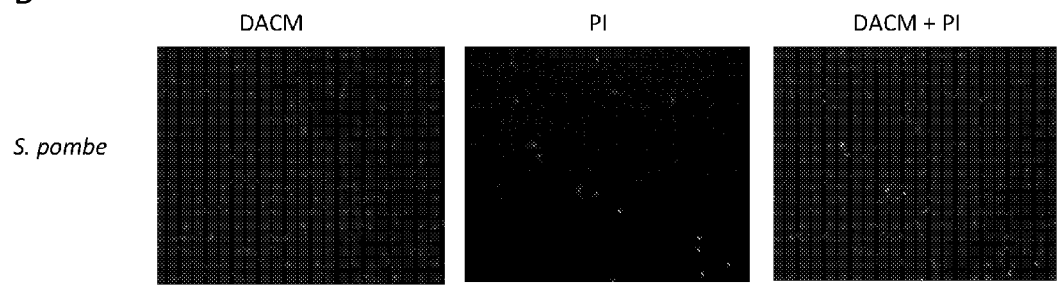
Figure 25:
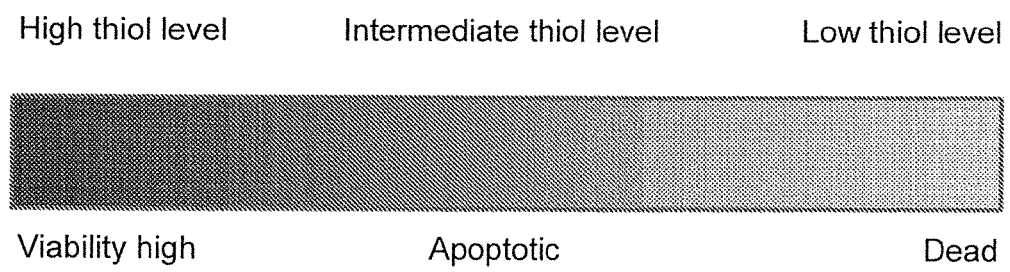
FIG. 25 is a diagram showing that cellular thiol level reflects a spectrum of viability.

Results. DCAM specifically stains living mammalian cells (examples 11, 15 and 16), probably by reacting with reduced peptide thiols. In order to evaluate whether DACM can be used for discriminating between living and dead yeast cells *S. pombe* and *S. cerevisiae* were stained with propidium iodide (PI) and DACM and immediately analysed by fluorescent microscopy. PI is a cell impermeant dye that only stains non-viable yeast cells with compromised plasma membranes. Fluorescent microscopy revealed that DACM preferable stains living yeast cells (FIG. 24, A and B). Thus, non-viable PI positive *S. pombe* and *S. cerevisiae* cells stain very weakly with DACM, whereas viable PI negative cells stain brightly with DACM.

Curiously, the majority of the fluorescent DACM apparently localizes to vacuoles in *S. pombe* and *S. cerevisiae* cells (FIG. 24, A). In conclusion, DACM can be used as a marker for measuring viability and vitality in yeast cells. Importantly, no incubation time is required using DACM. This is in contrast to other methods used for determining yeast viability, e.g. FUN1 (Invitrogen, #F7030), that requires up to 60 minutes of incubation prior to analysis.

The invention claimed is:

1. A method for quantitative or qualitative assessment of cell viability, comprising:
   providing a sample,
   adding (N-(9-acridinyl)maleimide (NAM) to said sample, reacting said NAM with said sample to selectively label viable cells so as to obtain a labelled sample,
   assessing cell viability in the labelled sample by quantitating labelled cells.

2. The method according to claim 1, wherein the sample is a biological sample.

3. The method according to claim 1, wherein the sample is selected from a body fluid sample, a tissue sample, a fermentation sample, a liquid cultivation sample, a cell culture sample, a water sample, a beverage sample, a pharmaceutical sample, a microelectronic product.

4. The method according to claim 1, wherein the sample is selected from a blood sample, a urine sample, a saliva sample, a semen sample, a solubilised tissue sample, a milk sample, a faeces sample, a tear sample.

5. The method according to claim 1, wherein the sample is selected from a liver sample, a kidney sample, a muscle sample, a brain sample, a lung sample, a skin sample, a thymus sample, a spleen sample, a gastrointestinal tract sample, a pancreas sample, a thyroid gland sample.

6. The method according to claim 1, wherein the sample is selected from a human sample, a mouse sample, a rat sample, a monkey sample, a dog sample.

7. The method according to claim 1, wherein the sample is selected from a bacterial culture, a mammalian cell culture, a protozoa culture or other cell cultures.

8. The method according to claim 1, wherein the sample is taken from raw material or environmental samples associated with processes associated with the manufacture, storage and transportation of said material.

9. The method according to claim 1, wherein the sample emits light after excitation from a light source for determination of viability.

10. The method according to claim 1, including a double labeling step wherein a dead cell labelling agent is also added to the sample.

11. The method of claim 1, further comprising assessing apoptotic status of the cells.

12. The method according to claim 1, wherein the sample is exposed to light before determination of viability.

13. The method according to claim 12, wherein the light originates from a thermal light source, a halogen lamp, or a gas lamp, a xenon lamp, a light emitting diode (LED), a laser or a laser diode.

14. A method for quantitative or qualitative assessment of biological cell viability, comprising:
   providing a sample comprising the biological cells to a sample domain,
   adding a labelling agent to said sample, wherein said labelling agent comprises (N-(9-acridinyl)maleimide (NAM), and reacting said labelling agent with said biological sample obtaining a labelled biological sample,
   exposing, onto an array of active detection elements, an at least one-dimensional spatial representation of electromagnetic signals having passed from the domain, the representation being one which is detectable as an intensity by individual active detection elements, under conditions which will permit processing of the intensities detected by the array of detection elements during the exposure in such a manner that representations of electromagnetic signals from the cells are identified as distinct from representations of electromagnetic signals from background signals, and wherein the spatial image exposed onto the array of active detection elements is subject to such a linear enlargement that the ratio of the image of a linear dimension on the array of detection elements to the original linear dimension in the exposing domain is smaller than 20:1,
   processing the intensities detected by the detection elements in such a manner that signals from the biological cells are identified as distinct from background signals, and based on the results of the processing obtaining a quantitative or qualitative assessment of the biological cell viability.

15. The method according to claim 14, wherein a light source is provided capable of emitting light to the labelled cells in the biological sample.

16. The method according to claim 15, wherein the light source is an LED light source.

17. The method according to claim 14, wherein the assessment of cells further includes assessing at least one of: metabolic activity, metabolite quantification, cell division, proliferation, health, stress level, apoptosis, necrosis or other state or condition.

18. A method for quantitative or qualitative assessment of cell viability of apoptotic cells, comprising:
   providing a sample,
   adding NAM to said sample, wherein said NAM comprises a group capable of reacting with one or several thiol groups in the cells,
   reacting NAM with said sample so as to obtain a labelled sample, assessing cell viability of apoptotic cells in the labelled sample.

19. The method of claim 18, further comprising assessing apoptotic status of the cells.

* * * * *